(12) United States Patent
Sherris et al.

(10) Patent No.: US 6,416,955 B1
(45) Date of Patent: Jul. 9, 2002

(54) EOSINOPHIL DEGRANULATING CONDITIONS

(75) Inventors: David Sherris; Eugene Kern; Jens Ponikau; Hirohito Kita, all of Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/553,790

(22) Filed: Apr. 21, 2000

Related U.S. Application Data

(60) Provisional application No. 60/130,603, filed on Apr. 22, 1999.

(51) Int. Cl.[7] .............................................. G01N 33/53
(52) U.S. Cl. ........................... 435/7.1; 435/4; 435/40.5; 435/40.52; 436/506; 436/507
(58) Field of Search ........................... 435/4, 7.1, 40.5, 435/40.52, 960; 436/506, 507

(56) References Cited

PUBLICATIONS

Manning et al. Laryngoscope. 1998. 108/10: 1485–1496. Abstract Only.*
Khan et al. J. Allergy and Clin. Immunol. 1994. 93 (1 Part 2): p236. Biosis Citation Only.*
Manning e tal. Laryngoscope. 1998. 108/10: 1485–1496.*
Erjefält et al., *J. Allergy Clin. Immunol.*, 1998, 102:286–294.
Keshavarian et al., *Gastroenterology*, 1985, 88(4):1041–1049.
Frigas et al., *Laboratory Investigation*, 1980, 42:35–43.
Frigas et al., *Mayo Clinic Proc.*, 1981, 56(5):345–353.
Gleich et al., *Annu. Rev. Med.*, 1993, 44:85–101.
Harlin et al., *J. Allergy Clin. Immunol.*, 1988, 81(5, Part 1):867–875.
Howarth, *Allergy*, 1995, 50(Suppl. 23):6–10.
Kaliner et al., *Otolaryngol. Head Neck Surg.*, 1997, 116(6, Part 1):S1–S19.
Lanza et al., *Otolaryngol. Head Neck Surg.*, 1997, 117(3, Part 2):S1–S7.
Lusk, *Otolaryngology Head Neck Surgery*, 3rd Edition, 1998, Ch. 8, pp. 104–115.
Mabry, *Otolaryngology Head Neck Surgery*, 3rd Edition, 1998, Ch. 48, pp. 902–909.
Masuyama et al., *Acta Oto–Laryngologica*, 1988, Supplement 458, 181–189.
McDowell et al., *Arch. Pathol. Lab. Med.*, 1976, 100(7):405–414.
Spurr, *J. Ultrastructure Research*, 1969, 26:31–43.
Wagner et al., *Am. J. Trop. Med. Hyg.*, 1998, 59:66–72.
Wasmoen et al., *J. Exp. Med.*, 1989, 170(6):2051–2063.
Wassom et al., *Mol. Immunol.*, 1979, 16(9):711–719.
Yang et al., *Rhinology*, 1995, 33(2):70–77.

* cited by examiner

*Primary Examiner*—Jennifer E. Graser
(74) *Attorney, Agent, or Firm*—Fish & Richardson P.C., P.A.

(57) ABSTRACT

The invention provides methods and materials related to the diagnosis of eosinophil degranulating conditions. Specifically, the invention provides methods and materials that involve visual types of analysis (e.g., microscopic analysis) that are used to determine the presence or absence of a horseshoe-shaped eosinophil granule structure within a mucus sample collected from a mammal. The presence of a horseshoe-shaped eosinophil granule structure within a patient's mucus indicates that the patient has an eosinophil degranulating condition. In addition, the invention provides methods and materials that involve immunological types of analysis (e.g., immunoassays) that are used to determine if a patient's mucus contains a tissue-damaging amount of eosinophil granule content that is outside the eosinophil granule and within the mucus. Like the presence of a horseshoe-shaped eosinophil granule structure, the presence of a tissue-damaging amount of eosinophil granule content outside the eosinophil granule and within the mucus indicates that the patient has an eosinophil degranulating condition. Further, the invention provides diagnostic kits that can be used to determine whether or not a patient has an eosinophil degranulating condition.

6 Claims, 20 Drawing Sheets

EOSINOPHIL DEGRANULATING CONDITIONS

RELATED APPLICATION

This application claims priority from U.S. Provisional Application Serial No. 60/130,603, filed Apr. 22, 1999.

BACKGROUND

1. Technical Field

The invention relates to methods and materials involved in the diagnosis of eosinophil degranulating conditions.

2. Background Information

Mucositis, the inflammation of mucosal tissue, is a serious medical problem that affects millions of people worldwide. For example, conservative estimates indicate that between 20 to 40 million Americans suffer from chronic rhinosinusitis, an inflammation of the nasal cavity and/or paranasal sinuses. In addition, chronic rhinosinusitis has been estimated to account for up to 90 percent of all cases of rhinosinusitis with acute rhinosinusitis (e.g., allergic rhinitis) accounting for the remaining 10 percent. While it is known that large numbers of eosinophils infiltrate the nasal tissue in patients with chronic rhinosinusitis as well as in patients with allergic rhinitis, the pathophysiology of these and other mucositis conditions remains unknown.

SUMMARY

The invention involves methods and materials related to the diagnosis of eosinophil degranulating conditions. Specifically, the invention provides methods that allow clinicians to determine whether or not a patient has an eosinophil degranulating condition. These methods involve visual types of analysis (e.g., microscopic analysis) that are used to determine the presence or absence of a horseshoe-shaped eosinophil granule structure within a mucus sample collected from a mammal. The presence of a horseshoe-shaped eosinophil granule structure within a patient's mucus indicates that the patient has an eosinophil degranulating condition. In addition, the invention provides methods that involve immunological types of analysis (e.g., immunoassays) that are used to determine if a patient's mucus contains a tissue-damaging amount of eosinophil granule content that is outside the eosinophil granule and within the mucus. Like the presence of a horseshoe-shaped eosinophil granule structure, the presence of a tissue-damaging amount of eosinophil granule content outside the eosinophil granule and within the mucus indicates that the patient has an eosinophil degranulating condition. The invention also provides diagnostic kits that allow clinicians to determine whether or not a patient has an eosinophil degranulating condition. Specifically, these kits contain a mucus collecting device and a fixative such that mucus samples can be analyzed microscopically. In addition, kits are provided that contain a binding reagent (e.g., an antibody) having binding specificity for an eosinophil granule molecule and a mucus collecting device. Additionally, kits are provided that contain a binding reagent having binding specificity for an eosinophil granule molecule and a mucolytic agent.

In one aspect, the invention features a method for diagnosing an eosinophil degranulating condition within mucus of a patient. The method includes providing a mucus sample from the patient, and determining whether or not the sample contains a horseshoe-shaped eosinophil granule structure. The presence of the structure indicates that the patient has the eosinophil degranulating condition. The condition can be a non-invasive fungus-induced mucositis condition such as non-invasive fungus-induced rhinosinusitis, non-invasive fungus-induced otitis media, and/or non-invasive fungus-induced bowel disease. The condition can be an asthma condition such as an asthma condition that is responsive to antifungal treatment. The condition can be chronic, and the patient can be a human or some other mammalian species (e.g., dog, cat, horse, etc.). The sample can include nasal mucus, middle ear mucus, bowel mucus, and/or sputum. The determining step can include microscopic analysis (e.g., electron microscopy).

In another embodiment, the invention features a method for diagnosing an eosinophil degranulating condition within mucus of a patient. The method includes providing a sample of mucus from the patient, and examining the sample to determine if mucus of the patient contains a tissue-damaging amount of eosinophil granule content that is outside the eosinophil granule. The tissue-damaging amount of the content outside the granule indicates that the patient has the eosinophil degranulating condition. The condition can be a non-invasive fungus-induced mucositis condition such as non-invasive fungus-induced rhinosinusitis, non-invasive fungus-induced otitis media, and/or non-invasive fungus-induced bowel disease. The condition can be an asthma condition such as an asthma condition that is responsive to antifungal treatment. The condition can be chronic, and the patient can be a human or some other mammalian species (e.g., dog, cat, horse, etc.). The sample can include nasal mucus, middle ear mucus, bowel mucus, and/or sputum. The content can contain major basic protein. The determining step can include an immunological analysis. For example, the immunological analysis can include (a) contacting the sample with a capture antibody to form a molecule-antibody complex where the content contains a molecule, and the capture antibody has specificity for the molecule, (b) determining the amount of the complex, where the amount of the complex indicates the amount of the content outside the granule, and (c) determining if the amount of the content outside the granule is the tissue-damaging amount.

In another aspect, the invention features a diagnostic kit containing an antibody and a mucolytic agent (e.g., N-acetyl-L-cysteine, dithiotlireitol, and recombinant human DNase). The antibody has specificity for a molecule from an eosinophil granule. The molecule can be major basic protein.

In another embodiment, the invention features a diagnostic kit containing an antibody and a mucus collector. The antibody has specificity for a molecule from an eosinophil granule. The molecule can be major basic protein. The mucus collector can be a brush, spatula, forceps, suction device, and/or suction bulb.

Another embodiment of the invention features a diagnostic kit containing a mucus collector, fixative, and instructions. The instructions indicate that the mucus collector is used to collect a sample of mucus from a patient, and that the fixative is used to fix the sample such that the sample can be examined to determine whether or not the patient has an eosinophil degranulating condition within mucus. The fixative can include Trump's fixative. The mucus collector can be a brush, spatula, forceps, suction device, and/or suction bulb.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
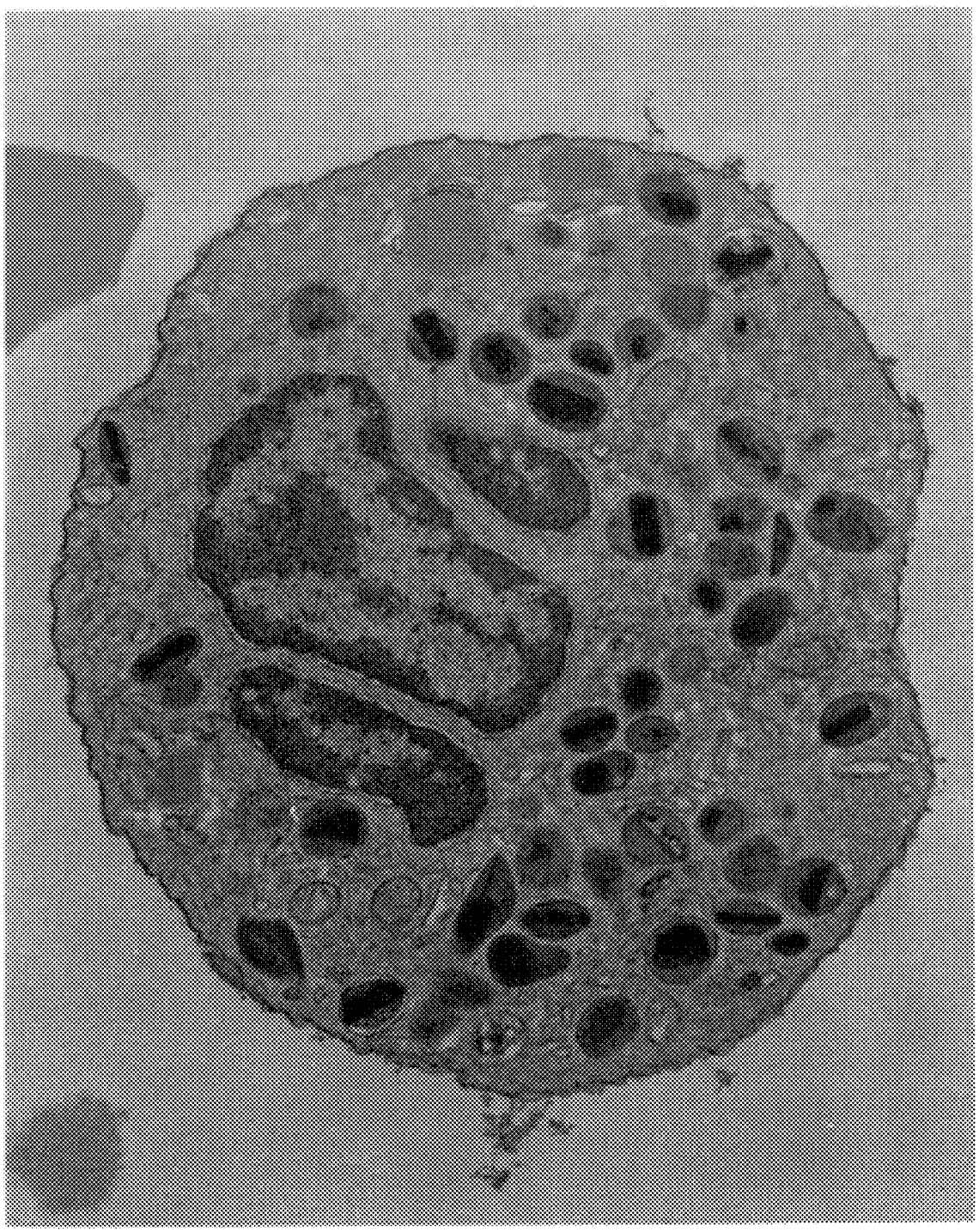
FIG. 1 is transmission electron microscope (TEM) micrograph depicting an eosinophil from a blood sample.

The invention involves methods and materials related to the diagnosis of eosinophil degranulating conditions. Specifically, the invention provides methods to determine whether or not a patient has an eosinophil degranulating condition. Such methods involve visual types of analysis (e.g., microscopic analysis) that are used to determine the presence or absence of a horseshoe-shaped eosinophil granule structure within a mucus sample collected from a mammal. The presence of a horseshoe-shaped eosinophil granule structure within a patient's mucus indicates that the patient has an eosinophil degranulating condition. The term "eosinophil degranulating condition" as used herein refers to conditions within a mammal's mucus that are characterized by the existence of degranulating eosinophils. Such conditions include, without limitation, non-invasive fungus-induced mucositis conditions and asthma conditions.

A non-invasive fungus-induced mucositis is defined as an inflammation of any mucosal tissue induced by a non-invasive fungal organism. Examples of mucosal tissue include, without limitation, the mucosa of the mouth, gut, nasal passages, paranasal sinuses, airways of the lung, trachea, middle ear, eustachian tube, vagina, and urethra. In general, an inflammation of a mucosal tissue can be-determined using any of the methods commonly known to a skilled artisan. For example, an individual can be identified as having an inflammation of a mucosal tissue upon examination of a tissue biopsy as well as by visual examination, endoscopic analysis, and image analysis techniques (e.g., X-rays, CT scans, and magnetic resonance imagery (MRI) scans) since the various inflamed mucosal anatomies tend to exhibit observable abnormal characteristics. Examples of non-invasive fungus-induced mucositis conditions include, without limitation, non-invasive fungus-induced rhinosinusitis, non-invasive fungus-induced otitis media, and non-invasive fungus-induced bowel disease (e.g., Crohn's disease and colitis).

Asthma can be characterized by a paradoxical narrowing of the bronchi (lung passageways) such that breathing becomes difficult. Individuals suffering from asthma can exhibit symptoms such as wheezing, difficulty breathing (particularly exhaling air), dyspnea, and tightness in the chest. Factors that can exacerbate asthma include rapid changes in temperature or humidity, allergies, upper respiratory infections, exercise, stress, and smoking. Individuals suffering from asthma can be identified using any of the known methods in the art. In general, asthma can be, without limitation, diagnosed objectively with a pulmonary function test (increased airway resistance) with or without provoking the airway (e.g., methacholine challenge test), chest X-rays, and auscultation of the chest. Examples of asthma conditions include, without limitation, asthma conditions that are responsive to antifungal treatment.

As described herein, a sample of mucus is collected from a patient and analyzed to determine whether or not the patient's mucus contains a horseshoe-shaped eosinophil granule structure. In general, mucus can be collected from any mucosal tissue by using a collection solution to flush the mucus-containing cavity. Proper mucus collection techniques should maximize recovery of a mucus-containing collection solution by allowing sufficient penetration of the appropriate anatomic cavities and by minimizing collection solution absorption by the individual. Vasoconstrictor agents can be used to maximize mucus collection and mucolytic agents can be used to dissolve obstructive mucus such that collection solution penetration is enhanced.

Before collecting a mucus sample, an individual can be treated with a vasoconstrictor agent and/or a mucolytic agent such that sufficient vasoconstriction and/or mucolytic action is induced in the appropriate region. Suitable vasoconstrictor agents can include, without limitation, phenylephrine hydrochloride (NEO-SYNEPHRINE®; Sanofi Pharmaceuticals), cocaine, and epinephrine. A mucolytic agent is any agent that liquefies mucus such that it can be recovered from the patient. Suitable mucolytic agents can include, without limitation, N-acetyl-L-cysteine (MUCOSIL™; Dey Laboratories) and recombinant human DNase (PULMOZYME®; Genentech, Inc.). Any administered vasoconstrictor agent or mucolytic agent should be allowed to take effect by waiting a sufficient period of time after administration such as about two to five minutes.

The following methods and materials can be used to collect a nasal-paranasal mucus sample. First, an individual is prepared to receive a collection solution in at least one nostril or nasal-paranasal cavity by directing the individual to inhale and to lower the chin, or in some other way constrict the access of fluids out of the mouth and down the esophagus. In a vertically sitting or standing individual, these maneuvers tend to minimize the loss or ingestion of the collection solution. Other maneuvers are also possible provided this goal is achieved. Second, an injection and collection system is configured. In general, the configuration is such that a collection solution can be administered to an individual's nostril and then efficiently collected in a container. The injection system can be, without limitation, a syringe with a curved blunt needle or tube assembly. The container can be any type of container that holds liquid. In addition, the container can be, without limitation, a storage container that is suitable for use as a transporter or sealable apparatus such that the collected sample can be handled or shipped. These containers also can contain an agent such as a preservative or antibacterial agent depending upon the desired use of the mucus sample. Third, a collection solution is administered into an individual's nostril and collected. Before administration, the individual can be instructed to expel the collection solution upon sensing the fluid in the nasal-paranasal anatomy. Alternatively, the individual can be instructed to expel the collection solution simultaneously with the administration. During administration, the collection solution can be forcibly injected into at least one nostril or side of the nasal-paranasal anatomy. The volume of the collection solution can vary according to the individual and the state of the mucositis. For example, fluid volumes can be, without limitation, between about 0.1 mL to about 100 mL or more, and specifically between about 0.1 mL and about 25 mL. The collection solution can be, without limitation, a saline solution, water, and any other suitable solution appropriate for contacting mucosal tissue. In addition, the collection solution can contain other agents that may be useful for the collection of mucus such as a mucolytic agent.

One goal of a collection solution is to dislodge and remove mucus within mucus-containing cavities. In addition to a collection solution acting as a natural flushing agent, the penetrating effect of a mucolytic agent within a collection solution can help liquefy thick obstructive mucus. Further, the combination of the force of administration with the near simultaneous pressurized expulsion by an individual can help dislodge and collect mucus. Typically, a collection solution can be administered during a period of less than about five seconds per side. In addition, a collection solution can be administered during a period of less than about three seconds. Alternatively, the time period of collection solution administration can be extend beyond five seconds depending on specific factors such as the degree of inflammation, the presence of obstructions, and the size of the individual. In addition, an administration greater than five second can be used when very small volumes or streams of collection solution are desired.

Other collection procedures also can be used to collect mucus samples, particularly if an individual is unable to comply or cope with a liquid collection procedure. Such additional procedures are well known in the art and include, without limitation, the surgical removal of mucus, a swab or mechanical mucus extraction procedure, and pressure or vacuum systems that extract mucus. In addition, these other collection procedures as well as the methods and materials described herein can be modified or adapted to obtain biological fluids from other areas of the body such as the middle ear and intestines.

Figure 2:
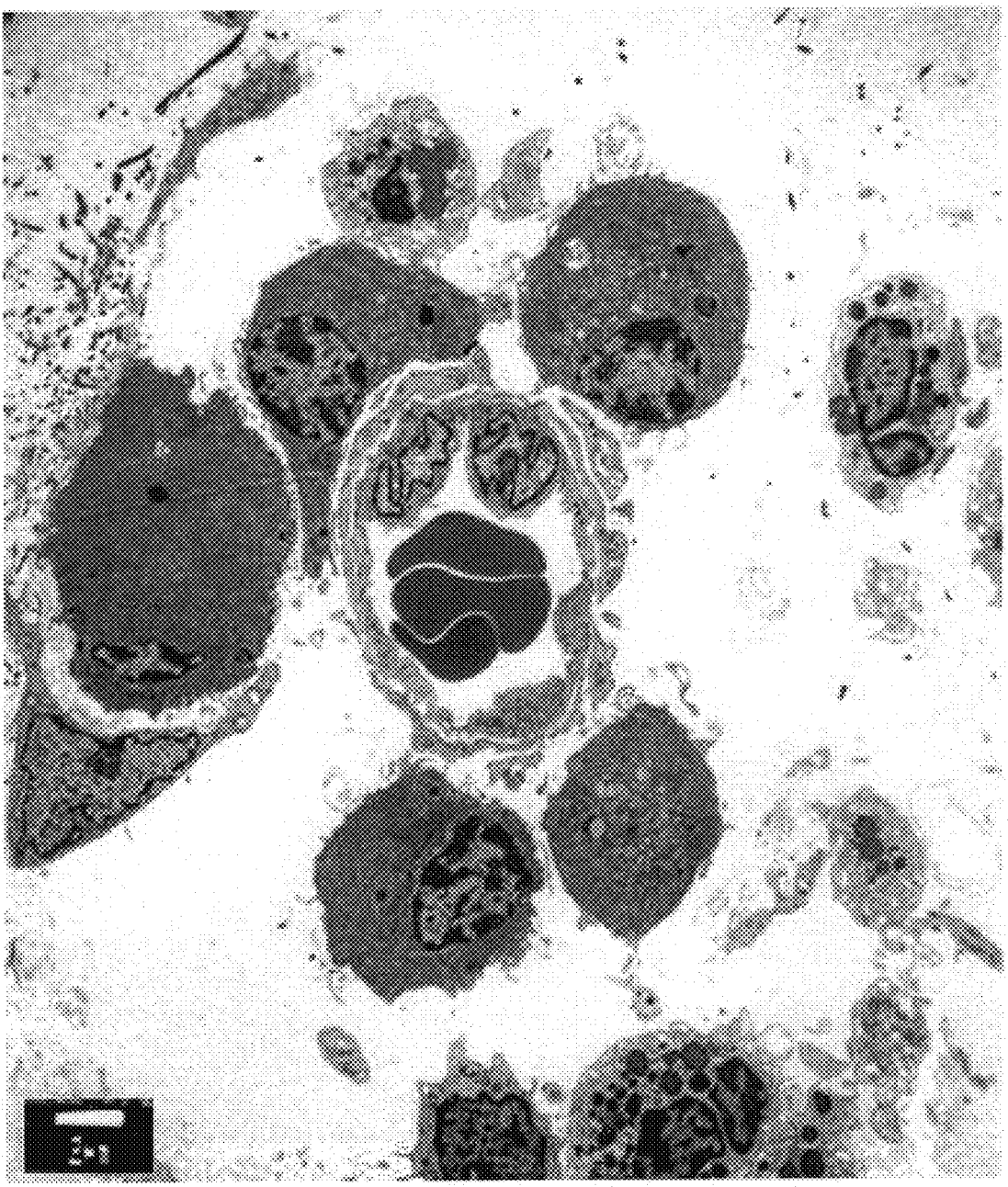
FIG. 2 is a TEM micrograph depicting T cells and eosinophils within tissue.
Figure 3:
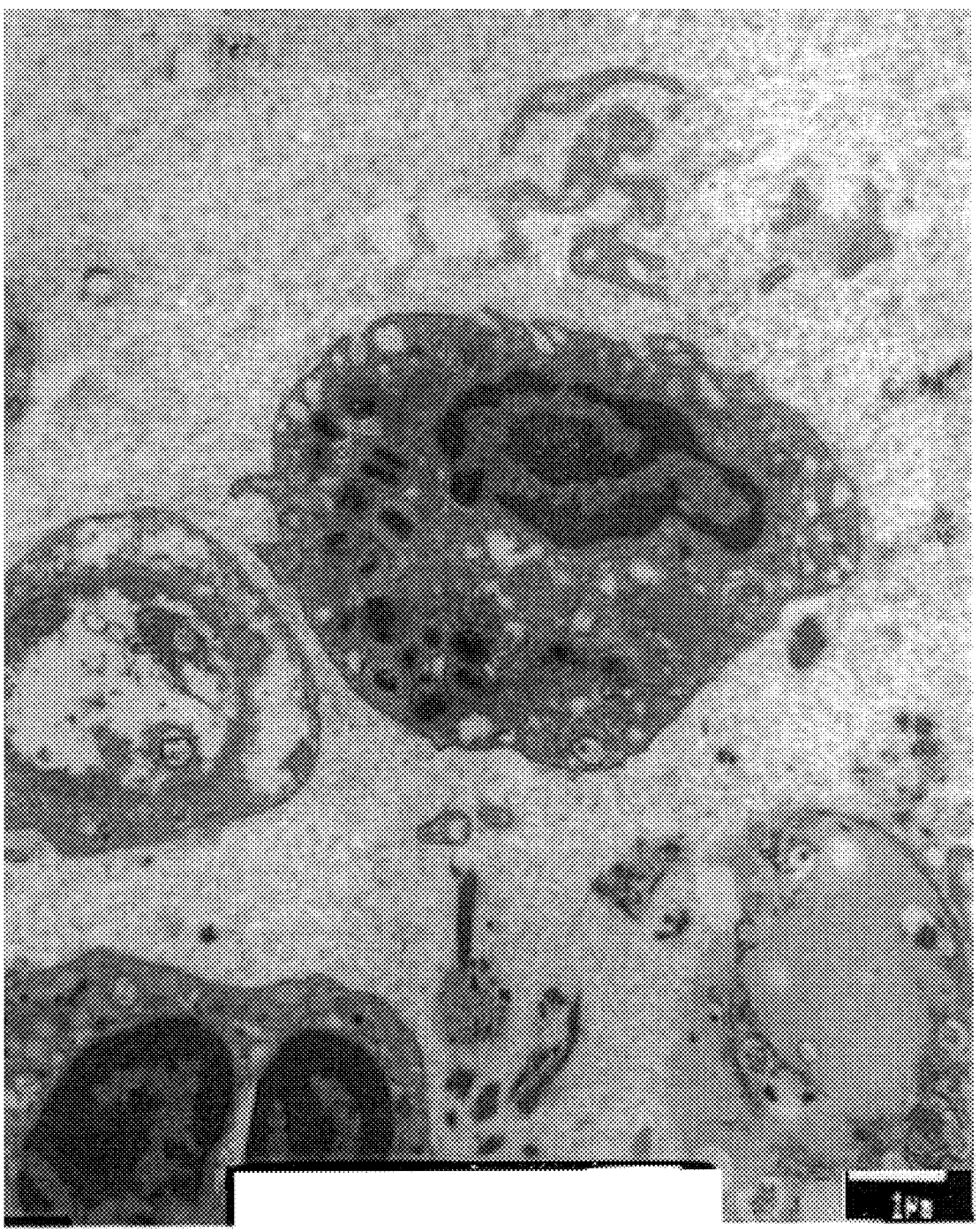
FIG. 3 is a TEM micrograph depicting an eosinophil within tissue.
Figure 4:
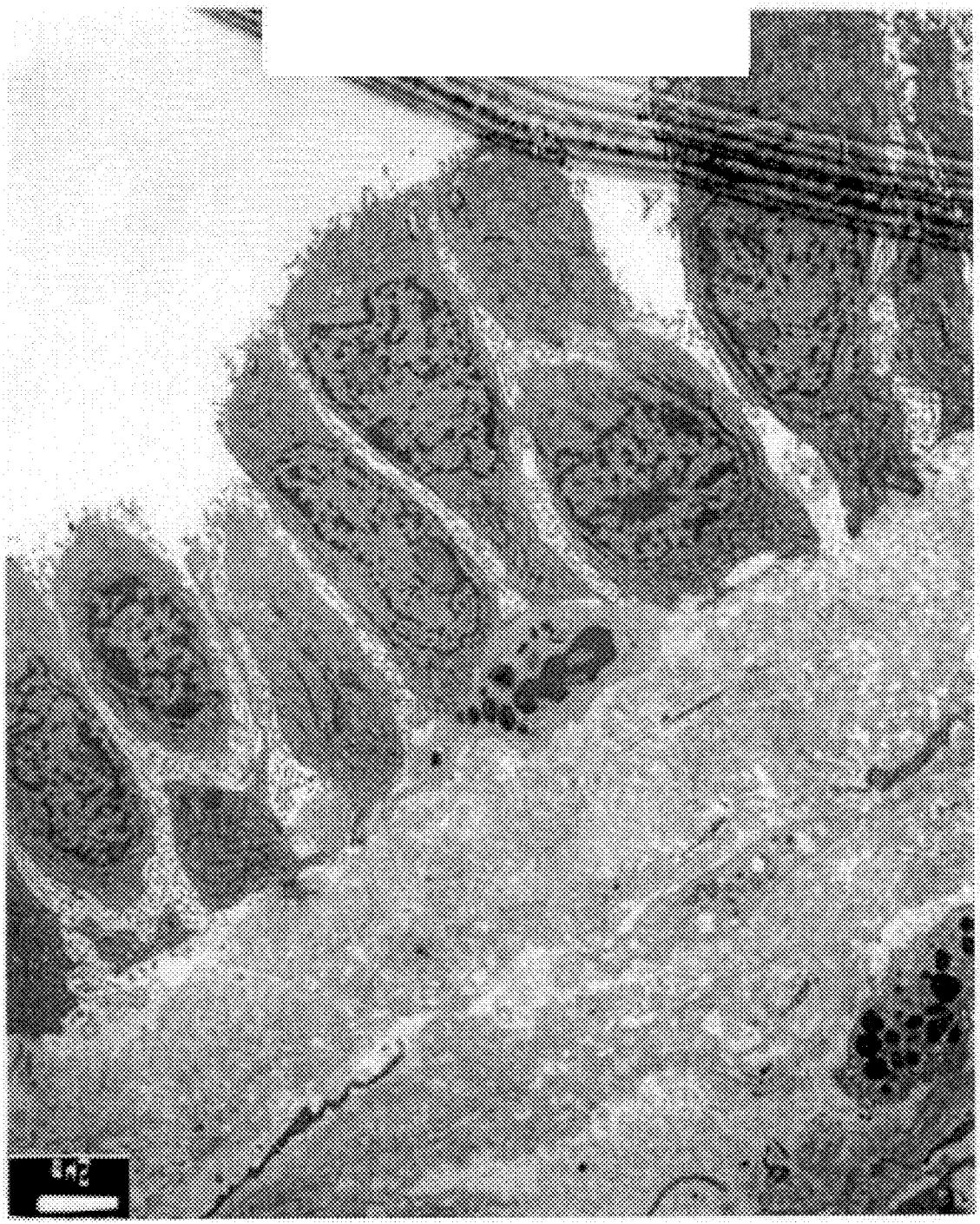
FIG. 4 is a TEM micrograph depicting an eosinophil about to migrate between epithelial cells.

Once collected, the mucus sample can be analyzed to determine whether or not the patient's mucus contains a horseshoe-shaped eosinophil granule structure. Typically, the mucus sample is examined by microscopy such as transmission electron microscopy (TEM). When in blood, eosinophils appear healthy and contain granules with crystalloid cores (FIG. 1). During mucositis conditions, eosinophils accumulate within the localized area of inflammation. To accumulate within a localized area, the eosinophils exit the blood stream and enter the tissue. FIG. 2 depicts several eosinophils within a tissue section as well as four T cells surrounding a blood vessel. Like blood eosinophils, eosinophils within tissue appear healthy and contain granules with crystalloid cores (FIG. 3). It is noted that a few eosinophils within tissue may degenerate. These degenerating eosinophils within tissue, however, rarely release their granule content. Once within tissue, eosinophils migrate toward the epithelial layer (FIG. 4). At the epithelial layer, the eosinophils leave the tissue and enter the mucus by migrating between epithelial cells, resulting in the accumulation of eosinophils within the mucus of patients with a mucositis condition.

Figure 5:
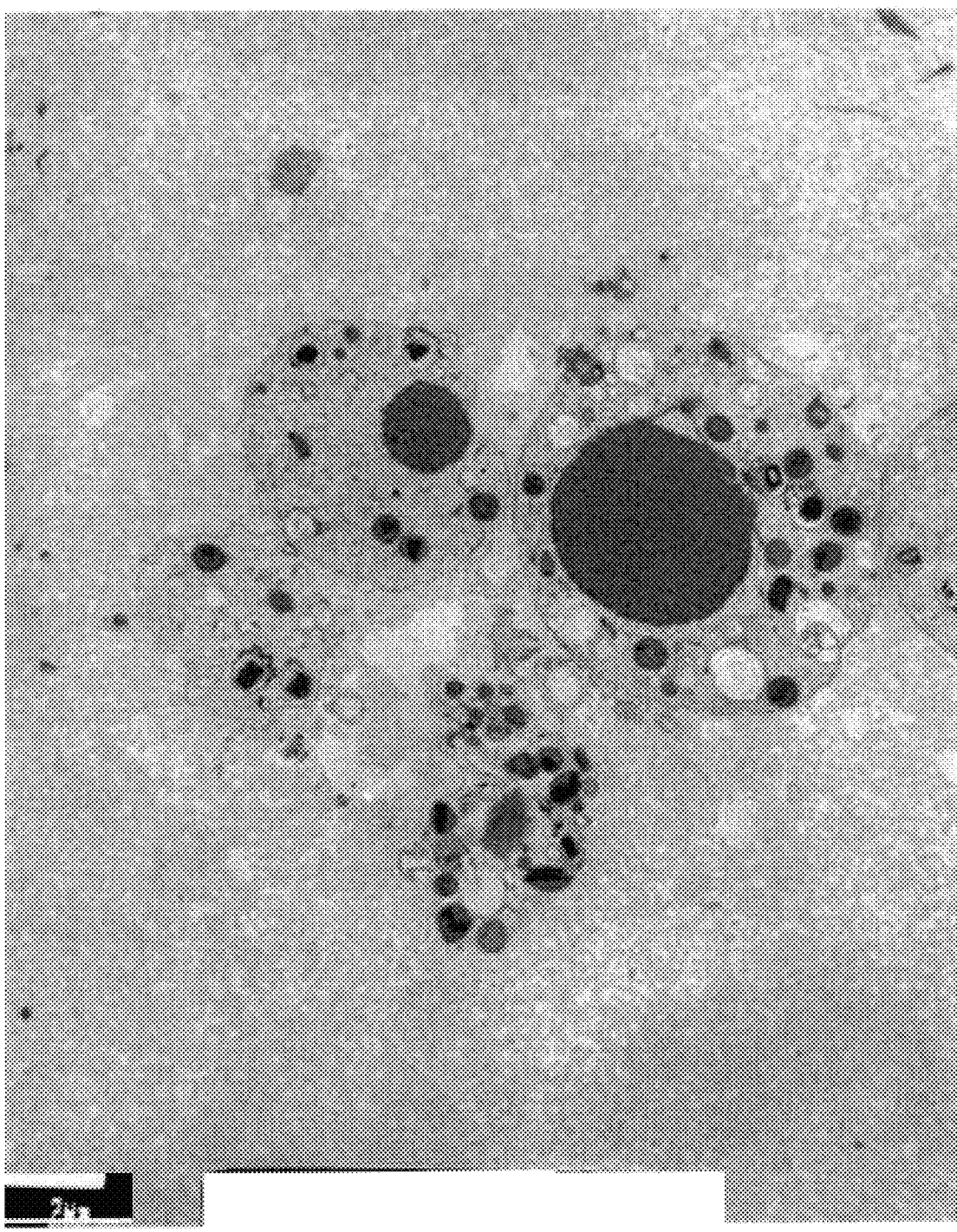
FIG. 5 is a TEM micrograph of a mucus sample from an allergic rhinitis patient depicting eosinophils within mucus.
Figure 6:
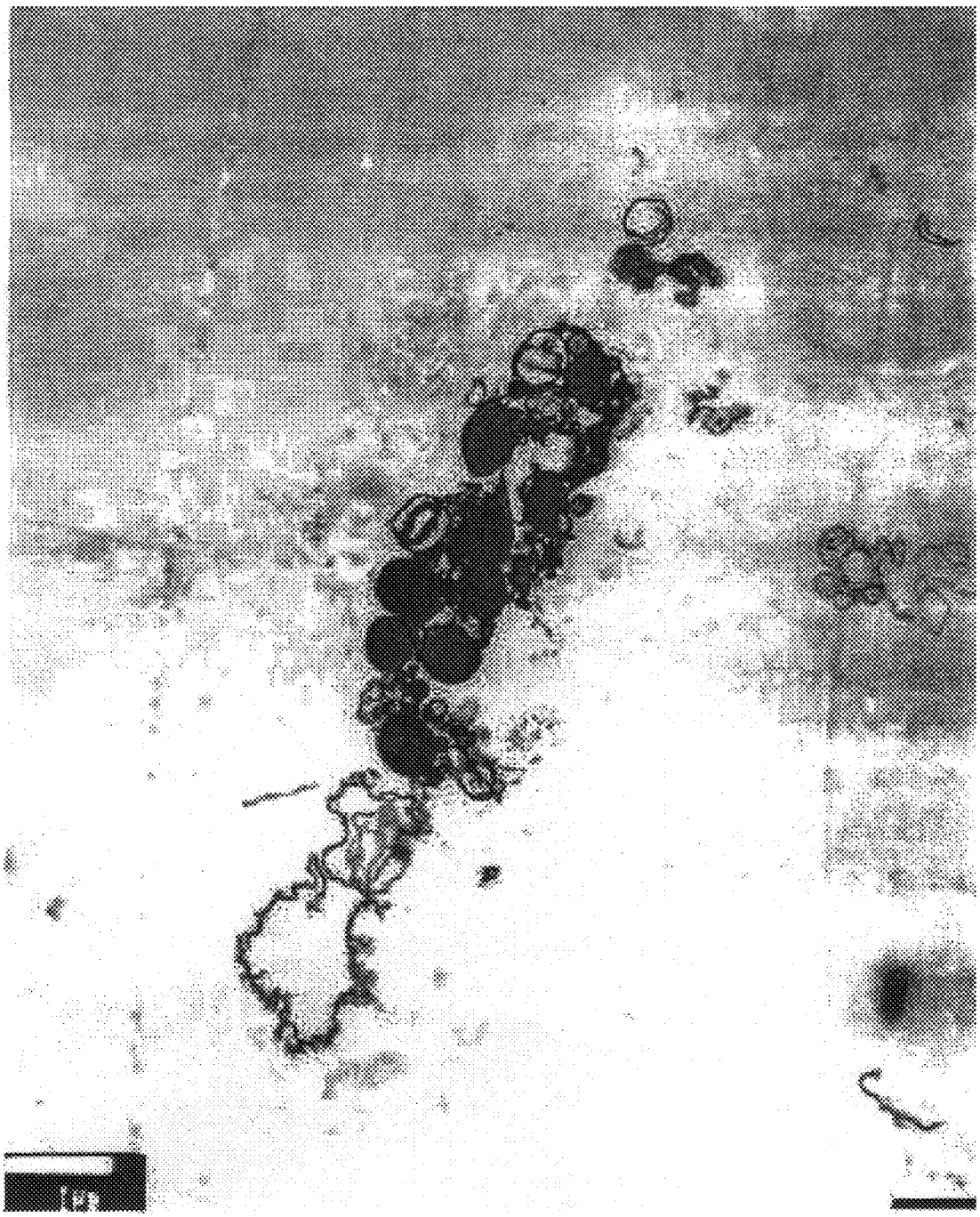
FIG. 6 is a TEM micrograph of a mucus sample from an allergic rhinitis patient depicting the remains of a degenerating eosinophils within mucus.
Figure 7:
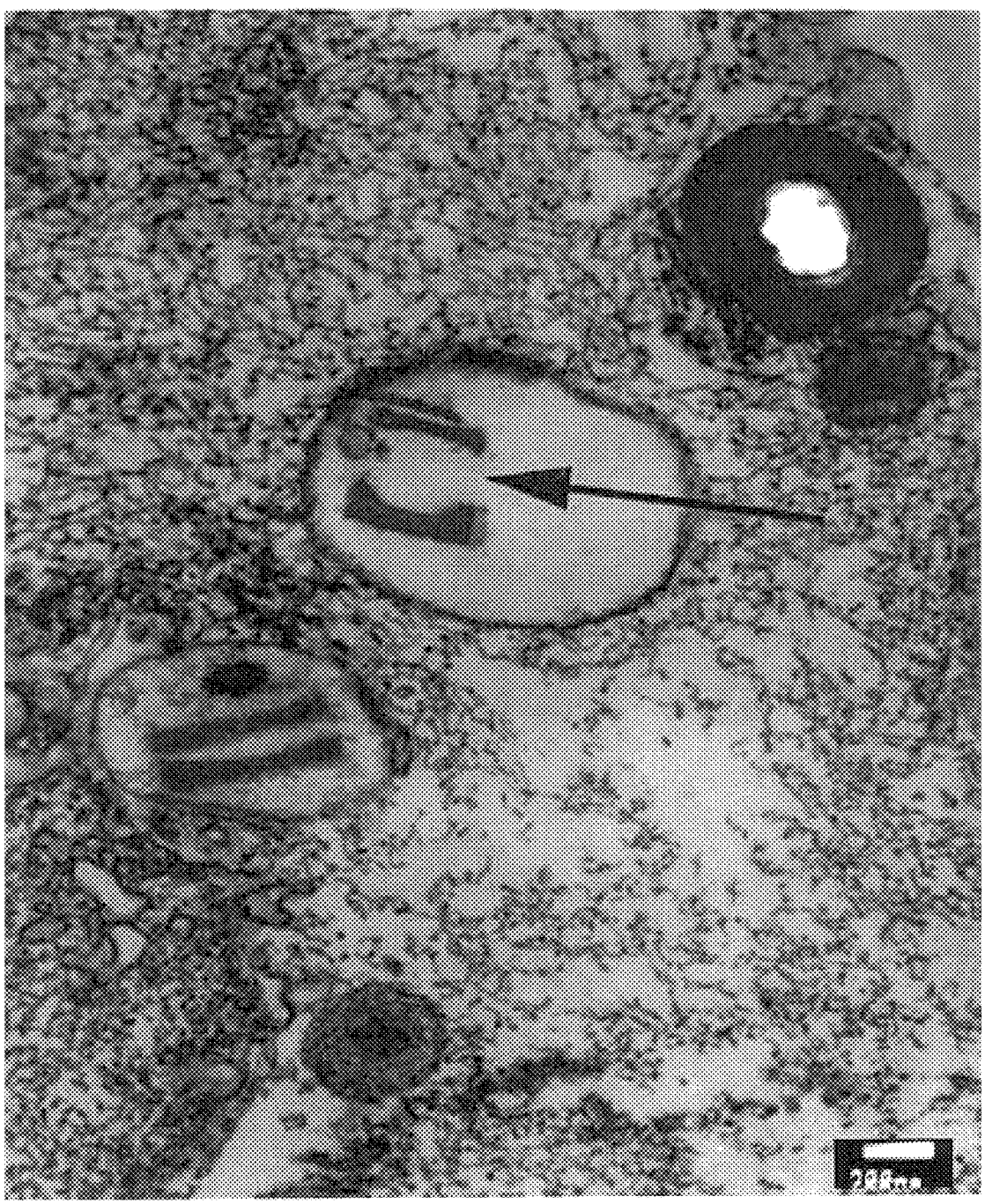
FIG. 7 is a TEM micrograph of a mucus sample from an allergic rhinitis patient depicting eosinophil granules of a degenerating eosinophil within mucus.
Figure 8:
FIG. 8 is a TEM micrograph of a mucus sample from an allergic rhinitis patient depicting an eosinophil granule of a degenerating eosinophil within mucus.
Figure 9:
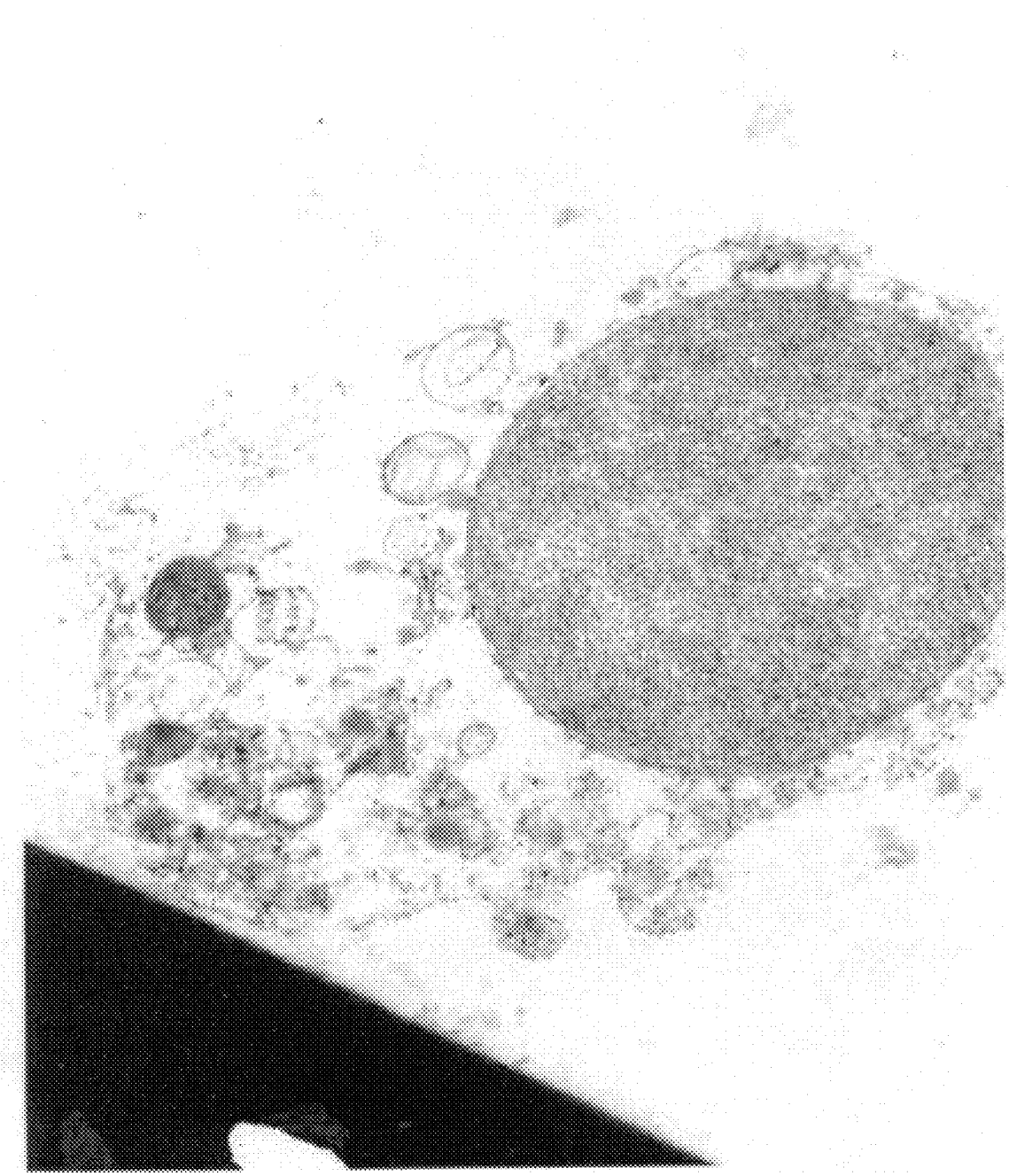
FIG. 9 is a TEM micrograph of a mucus sample from an allergic rhinitis patient depicting major basic protein (MBP) immunostaining of a degenerating eosinophil within mucus.

In allergic rhinitis, the eosinophils within mucus degenerate without degranulating (FIGS. 5–9). FIG. 5 depicts several eosinophils within a mucus sample collected from an allergic rhinitis patient. Each eosinophil is at a different stage of degeneration; however, none of the eosinophil granules have degranulated. Instead, the granule membrane of each granule remains completely intact, while the granule contents dissolve and the plasma membrane disappears (FIG. 6). Specifically, the crystalloid core loses its density, and the granule contents appear to dissolve from the inside to the outside without being released (FIGS. 7 and 8). These degenerating eosinophils within mucus contain immunoreactive MBP within their granules (FIG. 9).

Figure 10:
FIG. 10 is a TEM micrograph of a mucus sample from a chronic rhinosinusitis patient depicting eosinophils within mucus.
Figure 11:
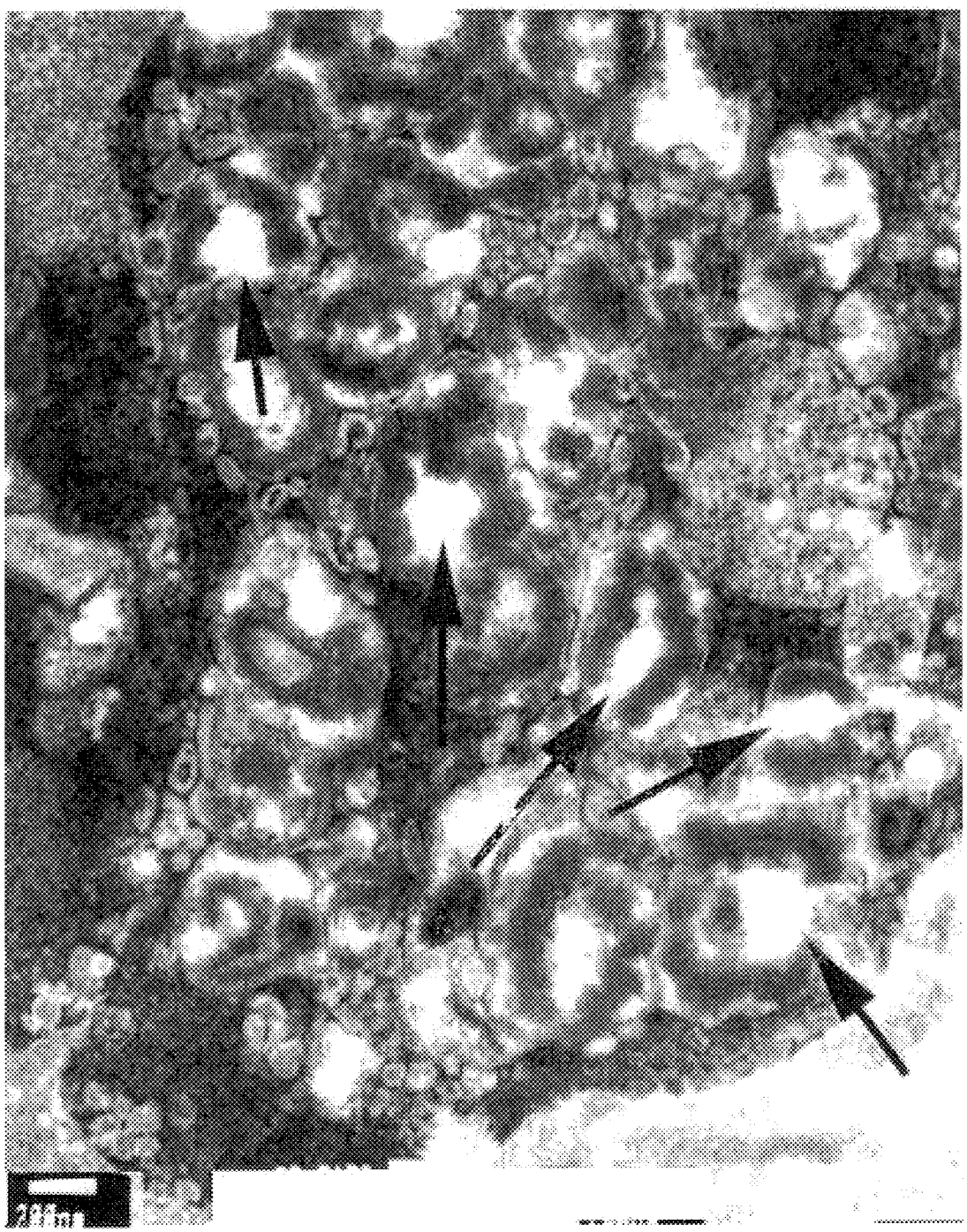
FIG. 11 is a TEM micrograph of a mucus sample from a chronic rhinosinusitis patient depicting eosinophil granules of an eosinophil within mucus.
Figure 12:
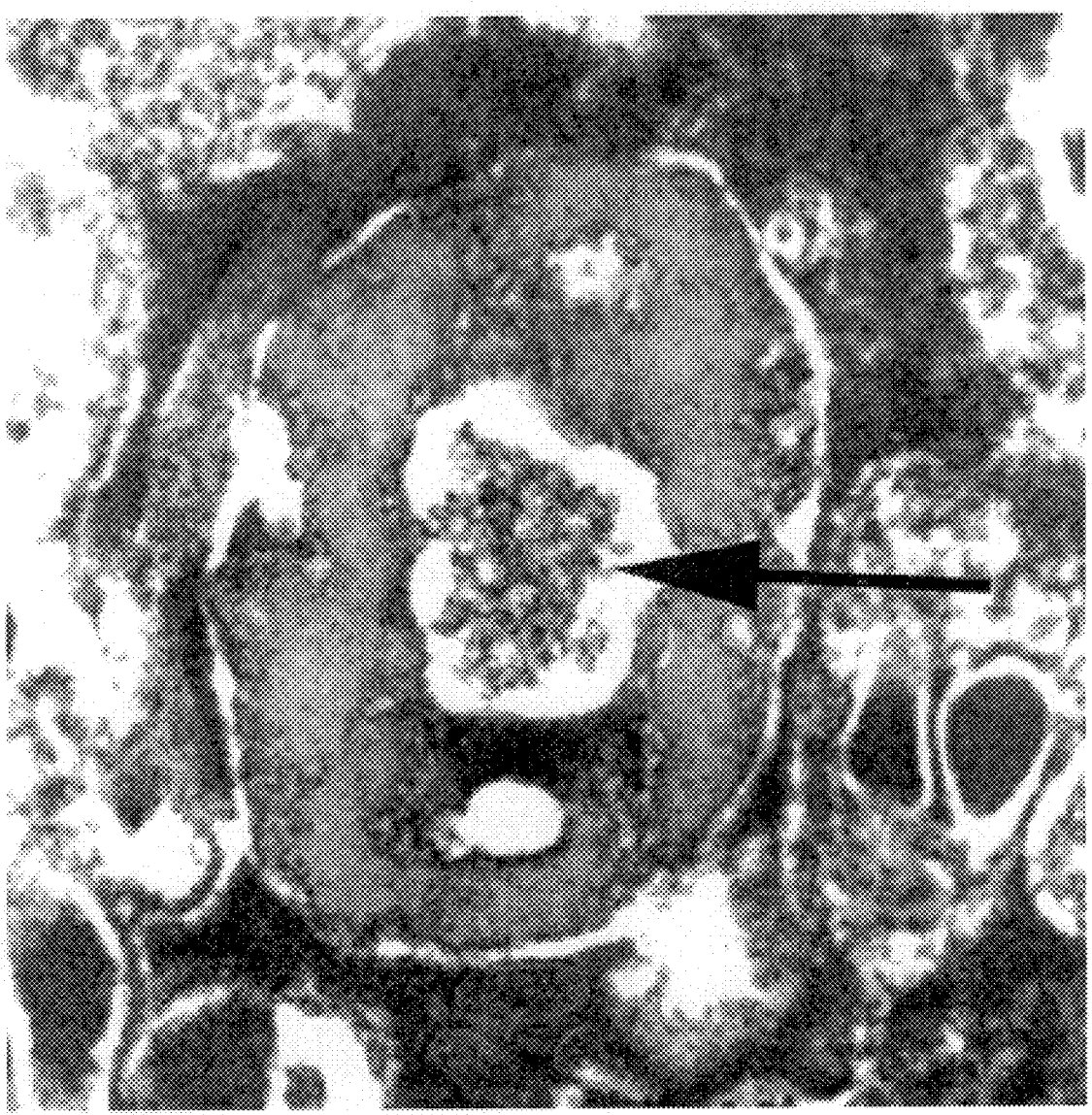
FIG. 12 is a TEM micrograph of a mucus sample from a chronic rhinosinusitis patient depicting a liquefying crystalloid core within an eosinophil granule of an eosinophil within mucus.
Figure 13:
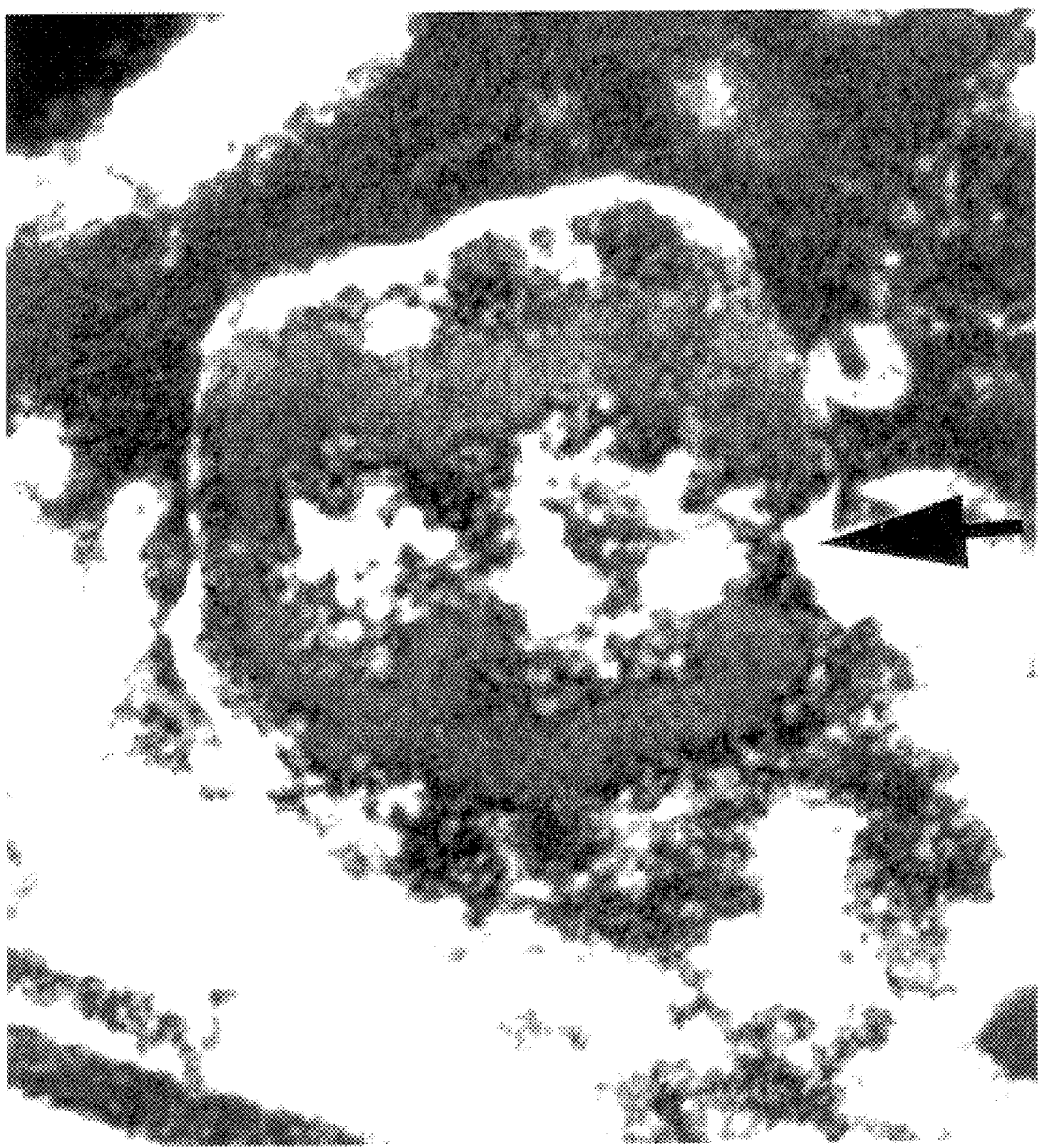
FIG. 13 is a TEM micrograph of a mucus sample from a chronic rhinosinusitis patient depicting a degranulating eosinophil granule of an eosinophil within mucus.
Figure 14:
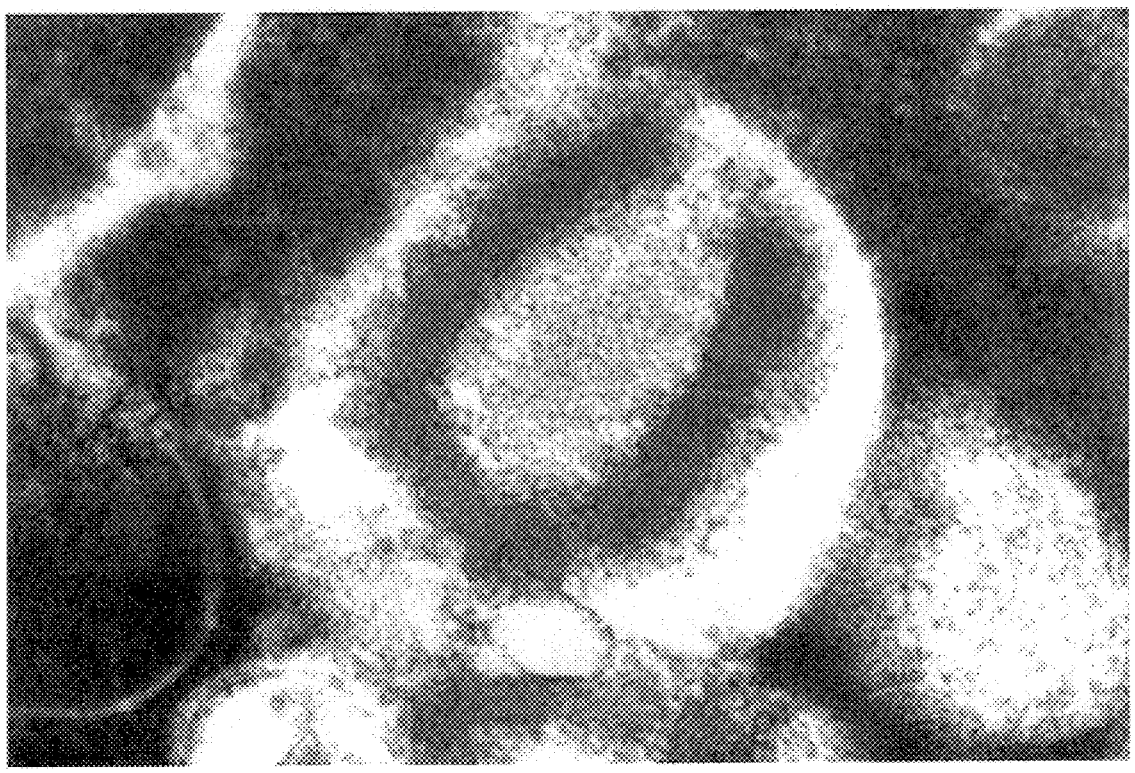
FIG. 14 is a TEM micrograph of a mucus sample from a chronic rhinosinusitis patient depicting a horseshoe-shaped eosinophil granule structure.
Figure 15:
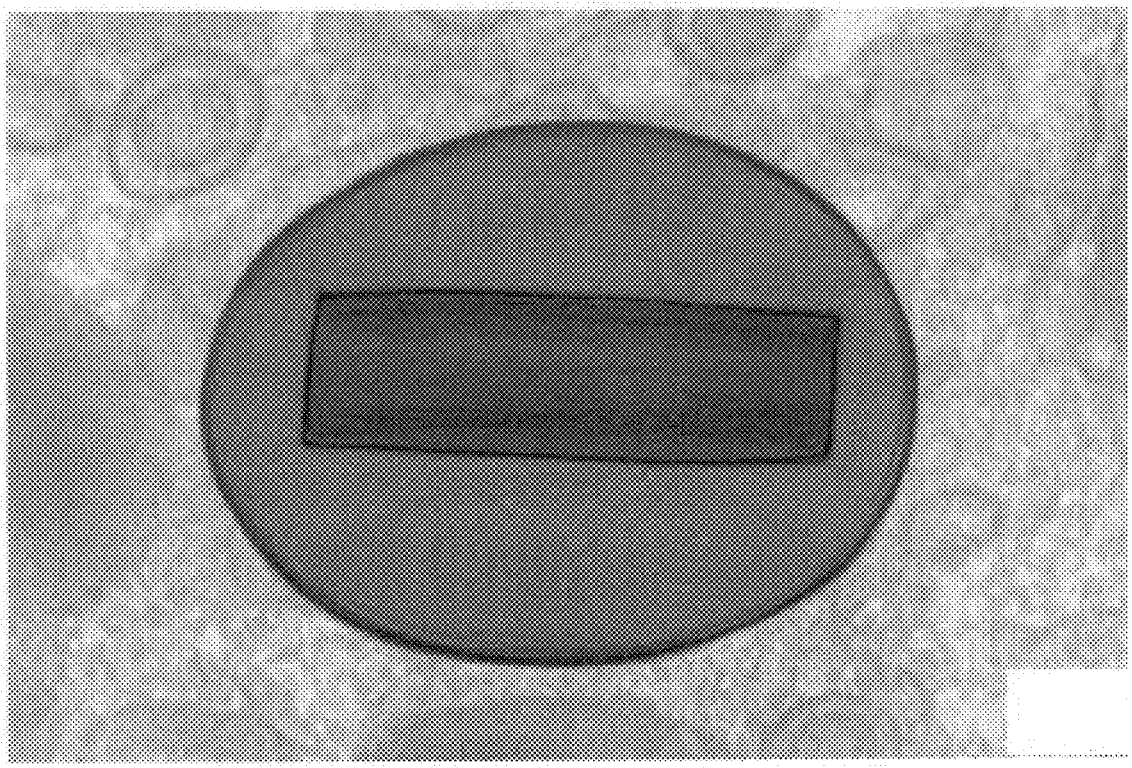
FIG. 15 is a diagram extrapolated from a TEM micrograph depicting the crystalloid core of a granule from an eosinophil within tissue.
Figure 16:
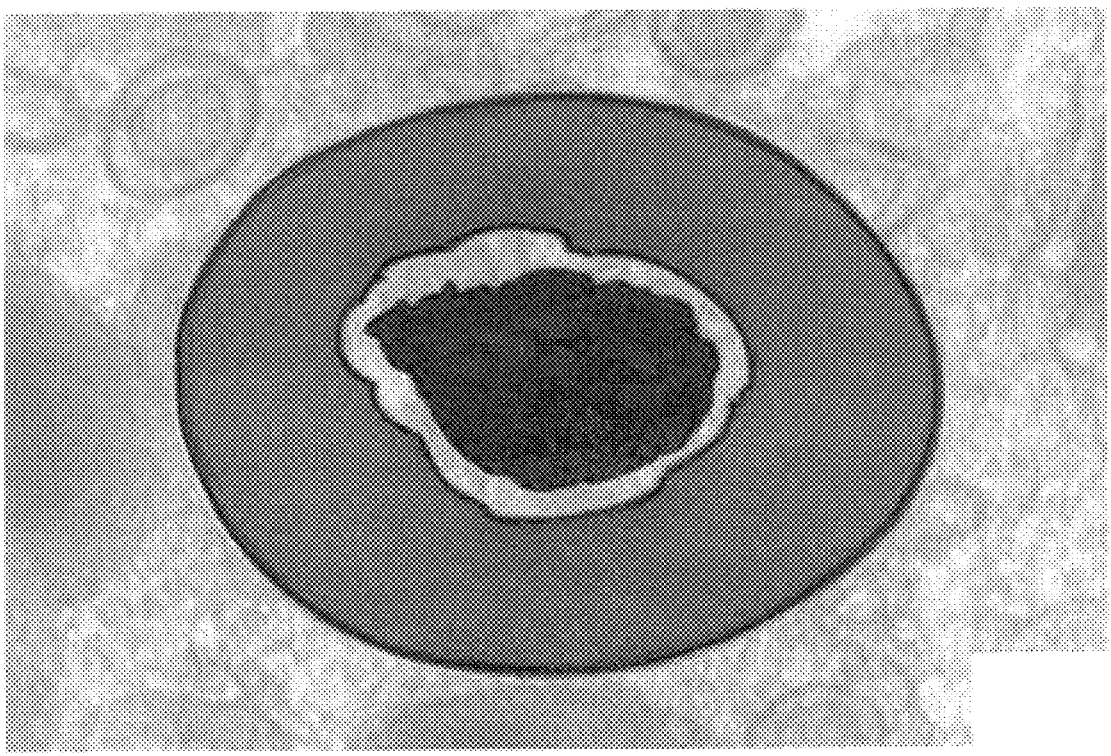
FIG. 16 is a diagram extrapolated from a TEM micrograph of a mucus sample from a chronic rhinosinusitis patient depicting a liquefying crystalloid core of a granule from an eosinophil within mucus.
Figure 17:
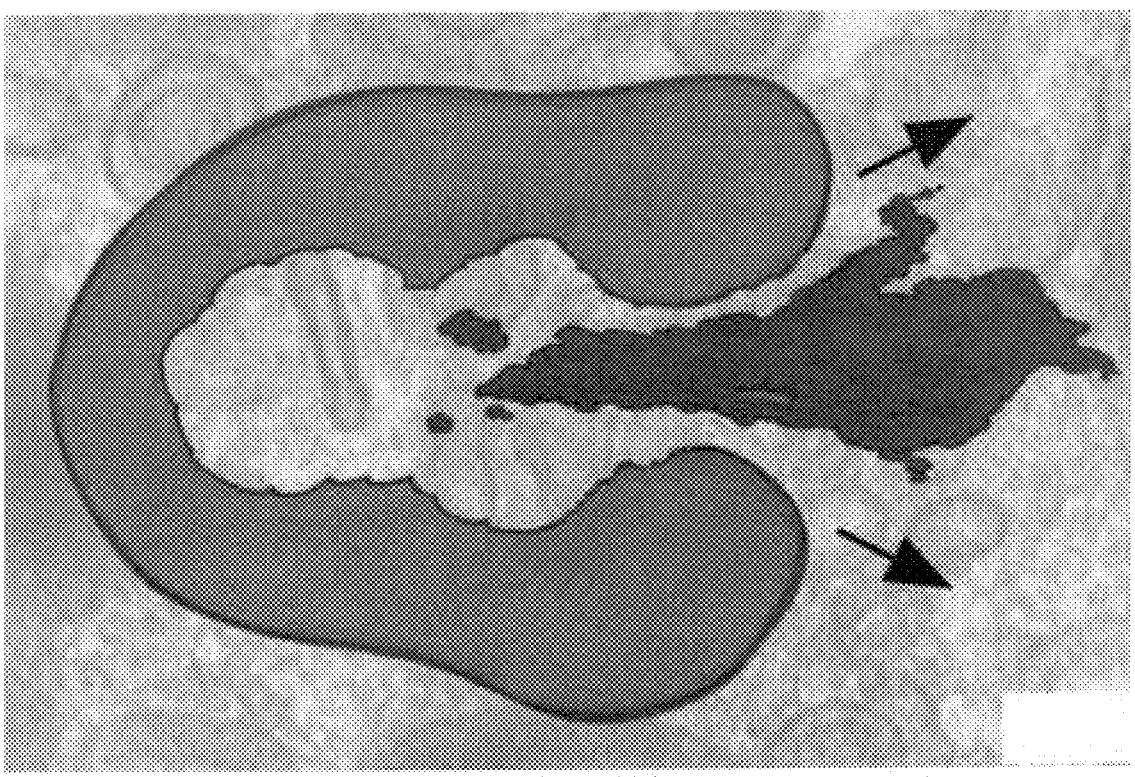
FIG. 17 is a diagram extrapolated from a TEM micrograph of a mucus sample from a chronic rhinosinusitis patient depicting the degranulation of a granule from an eosinophil within mucus.
Figure 18:
FIG. 18 is a TEM micrograph of a mucus sample from a chronic rhinosinusitis patient depicting MBP immunostaining of degranulating eosinophils within mucus.

In chronic rhinosinusitis, the eosinophils within mucus degranulate (FIGS. 10–18). FIG. 10 depicts several eosinophils within a mucus sample collected from a chronic rhinosinusitis patient. Each eosinophil contains many degranulated granules. Degranulated eosinophil granules were found to have a very striking horseshoe-shaped structure (FIG. 11). Before degranulating, the crystalloid core becomes diminished. The diminished crystalloid core is not dissolving as observed in allergic rhinitis patients, but rather the core appears to liquefy while the surrounding matrix remains intact (FIG. 12). This liquefied core then is released from the granule once the granule membrane opens (FIG. 13). The remaining eosinophil granule structure resembles a horseshoe (FIG. 14). This process of degranulation, which was observed to occur within eosinophils within the mucus of chronic rhinosinusitis patients and not allergic rhinitis patients, can be schematically depicted as shown in FIGS. 15–17. These degranulating eosinophils within mucus have released immunoreactive MBP that is observed both within the cell as well as outside the cell (FIG. 18).

As described herein, a mucus sample can be collected from a patient such as a patient with a mucositis condition, and that sample can be examined microscopically to determine whether or not horseshoe-shaped eosinophil granule structures are present. Again, the vast majority of eosinophil granules degranulate in eosinophil degranulating conditions such as chronic rhinosinusitis while few, if any, eosinophils degranulate in mucositis conditions such as allergic rhinitis. Any visual type of analysis can be used to identify horseshoe-shaped eosinophil granule structures including, without limitation, laser microscopy, electron microscopy, and high-powered light microscopy.

The invention also provides methods for diagnosing an eosinophil degranulatiing condition that involve immunological types of analysis (e.g., immunoassays) that are used to determine the presence or absence of a tissue-damaging amount of eosinophil granule content that is outside the eosinophil granule and within the mucus. Like the presence of a horseshoe-shaped eosinophil granule structure, the presence of a tissue-damaging amount of eosinophil granule content that is outside the eosinophil granule and within the mucus indicates that the patient has an eosinophil degranulating condition. The term "tissue-damaging amount" as used herein refers to the amount of granule content that, when in free form, causes damage to the epithelial cells within the body anatomy from which the mucus was collected. For the purpose of this invention, granule content is considered to be in free form once released from an eosinophil granule. The term "granule content" as used herein refers to any molecule contained within an eosinophil granule such as eosinophil cationic protein (ECP), eosinophil peroxidase (EPO), and major basic protein (MBP). As described herein, MBP appears to be the primary mediator of tissue damage in eosinophil degranulating conditions such as chronic rhinosinusitis, while other molecules such as EPO are also present within eosinophil granules. Thus, the amount of, for example, EPO can be measured to determine whether or not a particular person's mucus contains a tissue-damaging amount of granule content realizing that MBP, and not necessarily EPO, may be directly causing tissue damage.

In general, the amount of eosinophil granule content within the nasal/paranasal mucus of chronic rhinosinusitis patients is a tissue-damaging amount, while the amount within the nasal/paranasal mucus of allergic rhinitis patients is not. It is noted that the mucus from allergic rhinitis patients can contain an equivalent number of eosinophils as observed within the mucus from chronic rhinosinusitis patients. However, the eosinophil granule content within mucus from allergic rhinitis patients is contained within granules and not found within mucus in a free form. Thus, any method that can distinguish between free eosinophil granule content and granule content within a granule membrane can be used to diagnose eosinophil degranulating conditions. Such methods include, without limitation, immunological assays that use a binding agent (e.g., antibody, receptor, ligand, etc.) to detect free eosinophil granule content. Such binding agents include, without limitation, antibodies having specificity for MBP, EPO, and ECP. It will be appreciated that one skilled in the art could follow the teachings provided herein to devise a number of different immunological assays to detect eosinophil granule content in free form. For example, an anti-MBP antibody can be immobilized to a solid support, a mucus sample can be applied to the immobilized antibody such that any free MBP is captured, and a second labeled anti-MBP antibody can be used to detect any captured MBP. In these types of immunological assays, a simple color reaction can be used to identify mucus samples containing tissue-damaging amounts of free eosinophil granule content.

The invention also provides diagnostic kits that can be used to determine whether or not a patient has an eosinophil degranulation condition. Such kits can contain a mucus collecting device and a fixative such that mucus samples can be analyzed microscopically. The term "mucus-collecting device" as used herein refers to any type of device that can be used to collect mucus from a patient. For example, a brush, spatula, forceps, suction device, or suction bulb can be used to collect mucus from a patient. The term "fixative" as used herein refers to compositions that can be used to prepare mucus samples for microscopic analysis. For example, Trump's fixative can be used to prepare mucus samples for TEM analysis.

In addition, other diagnostic kits can contain a binding reagent (e.g., an antibody) having binding specificity for an eosinophil granule molecule and a mucus-collecting device. Such diagnostic kits can be used to determine the presence or absence of a tissue-damaging amount of eosinophil granule content that is outside the eosinophil granule and within the patient's mucus. The term "binding agent" as used herein refers to any molecule that has a binding specificity for another particular molecule. For example, a binding agent can be an antibody, receptor, ligand, or lectin. Other diagnostic kits can contain a binding reagent having binding specificity for an eosinophil granule molecule and a mucolytic agent. A mucolytic agent is any agent that can be used to dissolve mucus including, without limitation, N-acetyl-L-cysteine, recombinant human DNase, and dithiothreitol.

It will be appreciated that one skilled in the art could follow the teachings provided herein to devise various kits for the visual or immunological detection of eosinophil degranulating conditions. For example, immunological-based diagnostic kits can contain wash solutions. detection antibodies such that a color reaction indicates positive mucus samples, and the like.

The invention will be further described in the following examples, which do not limit the scope of the invention described in the claims.

EXAMPLES

Example 1

Chronic Rhinosinusitis Patients Have an Eosinophil Degranulating Condition

Tissue from chronic rhinosinusitis patients was examined using electron microscopy (n=9) and hematoxylin/eosin (H&E) staining (n=101). In these tissues, a large number of eosinophils were found migrating through the epithelium into the mucus. In every case, the examination of surgical waste from chronic rhinosinusitis patients revealed that the eosinophils were completely intact while migrating through the epithelium. Once outside the tissue and within the mucus, the eosinophils were found clustered around fungal organisms. Degranulation of the eosinophils was clearly observed by the marked deposition of free MBP around degenerating fungi. Immuno-histochemistry staining and immuno-electronmicroscopy of samples from chronic rhinosinusitis patients revealed that the MBP was located within intact cells and/or intact free granules while the eosinophils were within the tissue, but was set free in large amounts when the eosinophils were within the mucus.

While the eosinophils are within tissue, MBP was found to be located in the crystalloid core of eosinophil secondary granules. In contrast, the core was found to be liquified in the eosinophils located within mucus from chronic rhinosinusitis patients. In addition, the MBP was found to be released through an opening in the granule membrane. As described herein, the release of MBP within mucus results in the destruction of not only fungal organisms but also the nasal mucosa. The examination of the structure of eosinophils within mucus revealed that the empty granules exhibit a "horseshoe" appearance. These horseshoe-shaped eosinophil granule structures indicative of empty granules were present in every extramucosal eosinophil examined from patients with chronic rhinosinusitis.

Example 2

Allergic Rhinitis Patients do not Have an Eosinophil Degranulating Condition Tissue from allergic rhinitis patients also was examined using immuno-histochemistry staining and immuno-electronmicroscopy. In this study, the samples were taken from patients who had a positive history for allergic rhinitis as well as an elevated level of both total and specific IgE. In these allergic rhinitis patients, MBP was found to be located within intact eosinophils while within the tissue. In contrast to the eosinophil degranulation observed within the mucus of chronic rhinosinusitis patients, electron microscopy revealed that eosinophils did not degranulate within the mucus of allergic rhinitis patients (n=3). In fact, the granule membrane and core membrane remained intact while the cellular membrane was completely destroyed. These observations indicate that the eosinophil, through the release of a granule polypeptide MBP, induces inflammation and damage in chronic rhinosinusitis, but not in allergic rhinitis.

Example 3

Sample Size Needed for Statistical Significance

A power analysis determining the number of patients necessary to show statistical significance between two groups of patients was performed. Given the conservative assumption that eosinophils degranulate in 82.8 percent or more in the chronic rhinosinusitis group and degranulate in 36 percent or less in the allergic rhinitis group (odds ration 2.3:1 or higher), an 80 percent power was obtained with a probability of a type 1 error rate of 0.05. Thus, the number of patients needed for each group to demonstrate statistical significance between the two groups was found to be ten.

Example 4

Study Demonstrating Statistical Significance of Diagnosis

Ten patients with the clinical diagnosis of chronic rhinosinusitis and ten patients with the clinical diagnosis of allergic rhinitis are randomly selected to enter the study. The clinical diagnosis of allergic rhinitis is established by history, where the patients describe the typical signs of nose itching, sneezing, and clear rhinorrhea, and exhibit a positive skin test for allergy. The clinical diagnosis of chronic rhinosinusitis is established with a history of recurrent upper respiratory infections lasting for longer than three months and is confirmed with a routine coronal CT that demonstrates inflammatory mucosal thickening.

Each nostril is flushed with 20 mL of saline using a syringe with a curved blunt needle. The patient is instructed to take a deep breath and sneeze out the fluid while flushing. The return is collected and placed into centrifuge tubes with Trump's solution. The patient's clinic number is entered in a database together with the clinical diagnosis and a reference number. The centrifuge tubes are marked with the reference number, and sent directly to an electron microscopy (EM) laboratory.

Mucus is fixed in Trump's fixative (1% glutaraldehyde and 4% formaldehyde in 0.1 M phosphate buffer, pH 7.2) as described elsewhere (McDowell and Trump, *Arch. Path. Lab. Med.* 100: 405–414 (1976)). The specimen then are rinsed for 30 minutes in three changes of 0.1 M phosphate buffer (pH 7.2) followed by a one hour postfix in phosphate-buffered 1% $OsO_4$. After rinsing in three changes of distilled water for 30 minutes, the tissue is stained en bloc with 2% uranyl acetate for 30 minutes at 60° C. After en bloc staining, the tissue is rinsed in three changes of distilled water, dehydrated in progressive concentrations of ethanol and 100% propylene oxide, and embedded in Spurr's resin (Spurr, *J. Ultrastruct. Res.* 26:31–43 (1969)). Thin (90 nm) sections are cut on a Reichert Ultracut E ultramicrotome, placed on 200 mesh copper grids, and stained with lead citrate. Micrographs are taken on a JEOL 1200 EXII operating at 60 KV.

In a blinded fashion, clinicians are to examine carefully all the eosinophils in two randomly selected gridfields per patient under the EM, paying special attention to the granule morphology and granule crystalloid core in which the MBP is located. They are to study the morphology of the granules and determine the percent of cells containing either completely intact granule membranes or granule membranes having a horseshoe shape. The horseshoe shape granule membrane is observed when the granule is emptied and the MBP core has been released. Once all specimen are examined, the diagnosis is correlated with the EM findings.

Example 5

MBP Immunoradiometric Assay

Chloramine-T Method for Radiolabeling

In this technique, the oxidant chloramine T was added to a solution containing the antibody and $I^{125}$. The reaction was stopped by adding a reducing agent, sodium metabisulfite. The labeled antibodies were then separated from the free $I^{125}$ and reducing agent by gel filtration chromotagraphy. The reagents were: Chloramine-T; Sodium metabisulfite; 0.5 M $K_2HPO_4$—$KH_2PO_4$ buffer, pH 7.5; PPF-E buffer; AG1-X4 Anion exchange resin (50400 mesh); and $I^{125}$.

Reagent Preparation:

0.5M $PO_4$ buffer pH 7.5

| | |
|---|---|
| Na$_2$HPO$_4$ (0.5M × 16 L × 142 g/M) | 1136 g |
| KH$_2$PO$_4$ (0.5M × 3 L × 136.1 g/M) | 204.1 g |
| NaN$_3$ | 160 mL |

The base was titrated with the acid to pH 7.5 (about 2 L of KH$_2$PO$_4$).

| PPF-E buffer pH 7.5 | Stored at 0° C. |
|---|---|
| Defined bovine serum | 5 mL |
| 10% NaN$_3$ | 10 mL |
| 0.1M EDTA pH 7.5 | 100 mL |
| Protamine Sulfate | 1 g |
| Distilled H$_2$O | 685 mL |

The Protamine sulfate was added slowly to prevent clumping, and the resulting solution mixed well.

The AG1-X4 Anion exchange resin was saturated with 0.2 M PO$_4$ buffer and stored at 0° C.

Chloramine-T (1 mg/mL)

10 mg of Chloramine-T was weigh out and transferred to a 15 mL graduated screw top test tube. Then, 10 mL of 0.5 M PO$_4$ buffer was added just before reacting the polypeptide with the I$^{125}$.

Sodium metabisulfite (1 mg/mL)

10 mg of sodium metabisulfite was weigh out and transferred to a 15 mL graduated screw top test tube. Then, 10 mL of the 0.5 M PO$_4$ buffer was added just before reacting the polypeptide with the I$^{125}$.

Procedure:
A. The AG1-X4 column was prepared.
  1. mount a 3 mL syringe barrel on a ring stand
  2. pack a small amount of glass wool in the bottom
  3. pipet about 3 mL of the exchange resin into the column
  4. rinse with 15 mL of PPF-E buffer
  5. parafilm the top of the column
B. The Chloramine-T and Sodium metabislufite was weighed.
C. The radiation cooler was packed with the equipment and the prepared reagents.
  1. Chloramine-T and Sodium metabisulfite
  2. AG1-X4 column
  3. PPF-E buffer, about 30 mL
  4. 0.5 M PO$_4$ buffer pH 7.5, about 30 mL
  5. polypeptide to be labeled (keep on ice)
  6. small beaker of ice
  7. 10 numbered 12×75 mm test tubes in a rack (with caps)
  8. brinkman 1.5 mL vial for labeling reaction
  9. data sheet and/or notebook
  10. plastic pasture pipets and adjustable pipetman
  11. small lead pig
D. The radiolabeling was performed.
  1. Dilute Chloramine-T and Sodium metabisulfite to 1 mg/mL with 0.5 PO$_4$ buffer and mix well
  2. Set up equipment in the radiation safety hood: column, test tubes, reaction vial, buffers, etc.
  3. Pipet 25 RL of the PO$_4$ buffer, and 5 μL of I$^{125}$ (450–550 μCi, adjust if needed) into the reaction vial
  4. Record the counts in the reaction vial
  5. Add 10–30 μL of polypeptide to be labeled
  6. Add 10 μL Chloramine-T solution and allow to react for 45 seconds mixing gently using a 100 μL pipet and tip (save this tip)
  7. Next add 25 AL Sodium metabisulfite solution
  8. Transfer contents of the reaction vial to the column, rinse vial with PPF-E and add the rinses to the column (save vial and tip to count later)
  9. Collect fractions into the labeled tubes, rinsing with PPF-E buffer
     tube 1 about 1 mL
     tube 2 about 2 mL (this fraction contains most of the polypeptide peak)
     tubes 3–10 about 1 mL
  10. Count and record μCi of each fraction, tips. pasture pipet, and reaction vial Calculations:

Calculate the total amount of polypeptide in the peak saved and the μCi of I$^{125}$ incorporated (μCi/μg).

Major Basic Protein (MBP) of the eosinophil can be measured using an immunoradiometric assay. According to this procedure, the antigen to be assayed (MBP), was bound by a specific monoclonal antibody immobilized on a solid phase. In the second step, the amount of antigen bound was measured by its reaction with another monoclonal antibody of the same specificity radiolabelled with 125. The radioactivity counted is proportional to the amount of MBP bound by the first antibody.

Materials:
  NaCl, certified
  Trizma Base, reagent grade
  Na$_2$HPO$_4$, reagent grade
  KH$_2$PO$_4$, reagent grade
  Protamine Sulfate, grade x
  EDTA, certified, free acid
  Dithiothreitol, store desiccated, at 4° C.
  Iodaacetamide, store desiccated, at 4° C.
  TWEEN 20
  Defined Bovine Serum
  NaN$_3$
  Chloramine-T, Eastman Kodak
  Sodium Metabisulfite, A.C.S.
  KCl, A.C.S.

Reagent Preparation:
  1. Phosphate buffered saline (PBS) 10X

| | |
|---|---|
| KCl | 4 g |
| KH$_2$PO$_4$ | 4 g |
| Na$_2$HPO$_4$ | 22.9 g |
| NaCl | 160 g |

Dissolve in 2 liters distilled H$_2$O. Dilute this 1:10 with distilled H$_2$O for a working buffer concentration of 1X.

| 2. EDTA buffer 0.1M pH 7.5 | Stored at 0° C. |
|---|---|

37.2 g EDTA disodium salt (FW=372.25) dissolved in 1 liter distilled water.

| 3. Tris-EDTA buffer pH 8.1 | Stored at 0° C. |
|---|---|
| NaCl | 8.78 g |

-continued

| | |
|---|---|
| EDTA | 3.72 g |
| Trizmabase | 39.96 g |

Dilute to slightly less than 1 liter with distilled water and pH to 8.1. Check the pH again the next day. Add distilled water to one liter.

| 4. PPF-E buffer pH 7.5 | Stored at 0° C. |
|---|---|
| Defined bovine serum | 5 mL |
| 10% NaN$_3$ | 10 mL |
| 0.1M EDTA pH 7.5 | 100 mL |
| Protamine Sulfate | 1 g |
| Distilled H$_2$O | 685 mL |

Mix well using a magnetic stir plate. Best if Protamine Sulfate is added slowly to avoid clumping.

5. Washing buffer 14 L

| | |
|---|---|
| 0.5M PO$_4$ | 290 mL |
| TWEEN 20 | 147 mL |
| Distilled H$_2$O | 11600 mL |

6. 0.5 M PO$_4$ buffer pH7.5 Conductivity approximately 33,000

| | |
|---|---|
| Na$_2$HPO$_4$ (0.5M × 16 L × 142 g/M) | 1136 g |
| KH$_2$PO$_4$ (0.5M × 3 L × 136.1 g/M) | 204.1 g |
| NaN3 | 160 mL |

Titrate the base with the acid to pH7.5 (about 2 L of KH$_2$PO$_4$)

7. Dithiothreitol 0.1 M solution in Tris-EDTA

Weigh out only enough DTT for one assay. It cannot be stored, so must be made fresh each time 8. Iodoacetamide 0.02 M solution in Tris-EDTA Weigh out only enough for one assay. It must be made fresh each time.

9. 10%NaN$_3$ 10 g dissolved in 100 mL distilled H$_2$O

Calibration

Standard Preparation: The standard was pooled serum from patients with Hypereosinophilic syndrome that has been calibrated against purified, reduced, and alkylated MBP. A minimum of ten assays were performed using a MBP curve and several dilutions of the HES pool. The data from these assays were compiled and a derived value assigned to the HES pool in ng/mL. The standard curve for MBP was as follows:

A frozen aliquot of MBP of known concentration was thawed and diluted to 512 ng/mL in PPF-E buffer. Subsequent standard curve points were made as follows:

256 ng/mL 0.5 mL of 512 ng/ml+0.5 mL of PPF-E buffer
128 ng/mL 0.5mL of 256 ng/ml+0.5mL of PPF-E buffer
64 ng/ml 0.5 mL of 128 ng/ml+0.5mL of PPF-E buffer
32 ng/mL 0.5 mL of 64ng/ml+0.5mL of PPF-E buffer
16 ng/mL 0.5 mL of 32 ng/ml+0.5mL of PPF-E buffer
8 ng/mL 0.5 mL of 16 ng/ml+0.5mL of PPF-E buffer
4 ng/mL 0.5 mL of 8 ng/ml+0.5mL of PPF-E buffer
2 ng/mL 0.5 mL of 4 ng/ml+0.5 mL of PPF-E buffer
1 ng/mL 0.5 mL of 2 ng/ml+0.5 mL of PPF-E buffer The calibrated HES pool was used as the standard for all test assays. It must first be reduced and alkylated (as do all samples) and the dilution of this step calculated in the final dilution for curve point; i.e., the calibrated concentration of HES pool was 22,000 ng/mL. 22,000/4.4 (the dilution factor of the reduction and alkylation) gives a final concentration of 5000 ng/mL. This is further diluted for a curve point of 256 ng/mL. The standard curve dilution was as such:

128.0 ng/ml 0.5 mL of 256 ng/ml+0.5 mL of PPF-E buffer
64.0 ng/ml 0.5 mL of 128 ng/ml+0.5 mL of PPF-E buffer
51.2 ng/ml 100 ul of 256 ng/ml+400 ul of PPF-E buffer
32.0 ng/ml 0.5 mL of 64 ng/ml+0.5 mL of PPF-E buffer
25.6 ng/ml 50 ul of 256 ng/ml+450 ul of PPF-E buffer
16.0 ng/ml 0.5 mL of 32 ng/ml+0.5mL of PPF-E buffer
8.0 ng/ml 0.5mL of 16ng/ml+0.5mL of PPF-E buffer
4.0 ng/ml 0.5mL of 8ng/ml+0.5ml of PPF-E buffer Quality Control Normal control: serum from a normal patient High control: pooled serum from HES patients not included in the standard HES pool.

Large batches of each control were collected and stored at −20° C. in 74 μL aliquots. A normal control and high control were included in every assay at two dilutions each. A 1:5 and 1:50 dilution for the normal control and a 1:100 and 1:200 dilution for the high control was used. All dilutions were made in PPF-E buffer after the samples were reduced and alkylated. Control data was collected over several assays; and mean, range, and standard deviation information were calculated. These values were readjusted from time to time. If both controls were out of range, the assay was repeated.

Quantitative Testing Procedure:

A. Prepare enough of the capture monoclonal antibody (J146B6 stored at 4° C. in PBS with 1% NaN$_3$) to coat Immulon 4 removawell strips for the entire assay.
  1. Coating concentration is 10 μg/mL in PBS. Add 100 μL/well.
  2. Allow strips to shake gently at room temperature on a mini shaker for two hours or overnight at 4° C.
  3. Aspirate dry and add 100 μL/well of the PPF-E buffer, shake one hour at room temperature. At this step the strips may be stored covered and frozen at −20° C. to be used at a later time.

B. Sample preparation: reduction and alkylation
  1. Label 10×75 mm glass test tubes; one for each sample, controls and standard HES serum pool.
  2. Pipette 50 μL of each sample, control, and standard HES pool into the above labeled tubes.
  3. Next add 130 μL of the Tris-EDTA buffer, pH8 to each tube.
  4. Add 20 μL of a freshly prepared 0.1 M DTT solution.
  5. Vortex briefly and incubate at room temperature for one hour.
  6. Next add 20 μL of a freshly prepared 0.02 M Iodoacetamide solution.
  7. Vortex briefly, after 20 minutes, the reaction should be completed.
  8. During incubation periods, prepare 10×75mm glass test tubes for dilutions of the reduced and alkylated samples, controls, and standard HES curve.
  9. Dilute the reduced and alkylated samples, controls, and standard HES curve in PPF-E buffer.

C. Aspirate PPF-E buffer from the wells.
D. In duplicate, pipette prepared standard curve, diluted controls and samples at 100 μL/well
  1. Every 96 well plate should include a duplicate blaik (PPF-E), normal and high controls.
  2. The standard curve is included on every other 96 well plate and each point in duplicate.
E. Shake gently at room temperature for one and a half hours or longer.
F. Aspirate wells dry and wash five times with the washing buffer. A plate washing apparatus works well for this.
G. Add 100 μL/well of prepared $I^{125}$ radiolabelled monoclonal antibody.
  1. J14-8A2 is radiolabelled with $I^{125}$ using the Chloramine-T method
  2. Dilute the radiolabelled antibody to a working concentration of 50 ng/mL in PPF-E buffer. Do this in the hood.
H. Shake gently for one and a half hour or longer at room temperature. It may go overnight at 4° C.
I. Remove radiolabel by aspirating into a radioactive waste container in the hood.
J. Wash wells five times with the washing buffer.
K. Count wells in a gamma scintillation counter for one minute.

Radiometric Measurements:
A. A gamma scintillation counter for $I^{125}$ is used according to the manufacturer.
B. A protocol is used to count and convert the counts per minute data into number values.

Data Calculation:
A. Curve fit is defined by polynomials joined at standard points using a smoothing factor. Criteria imposing only one inflection point and no extreme values for the standard curve points.
B. A worklist is entered for each assay. This includes the sample identification and the dilution factor of that sample or control.
C. Controls and samples are read off the standard curve and multiplied by the appropriate dilution factor. Duplicate points are calculated separately and then resulting values averaged.

Reporting Results:
A. Assay is valid if standard curve meets instrument parameters and if controls are within the standard deviation limits established.
B. If the counts per minute of any sample should fall above the second highest standard curve point, that sample must be repeated at a higher dilution.
C. If the counts per minute of any sample should fall below the lower point of the standard curve, that sample must he repeated at a lower dilution or no dilution, whatever is most likely to put that sample within the best fit of the standard curve.
D. Normal values and ranges are included.
E. Samples are reported in ng/ml without a decimal point.
F. Values which are below the standard curve, without dilution, are reported as below detection or less than 45 ng/mL.

Example 6

Chronic Rhinosinusitis Patients Have an Eosinophil Degranulating Condition as Determined by an Immunoassay Mucus samples collected from chronic rhinosinusitis patients and normal controls were examined using the MBP assay described in Example 5. It is noted that other MBP assays can be used such as those described elsewhere (Wassom et al., *Molec. Immunol.* 16:711–719 (1979); Frigas et al., *Mayo Clin. Proc.*, 56:345–353 (1981); and Wasmoen et al., *J. Exp. Med.*, 170:2051–2063(1989)). First, direct suctioning was used to collect mucus samples from the nasal cavities and sinus cavities of chronic rhinosinusitis patients as well as from the nasal cavities of normal controls. The minimum amount of mucus sample collected from each patient was about 0.5 mL. Once collected, an equal volume of 0.15 M NaCl was added to each sample. The resulting solution was then gently mixed with a vortex mixer for no more than 30 seconds. Once mixed, the samples were centrifuged at 40,000*g for 20 minutes. After centrifugation, the supernatants were collected, reduced with dithiothreitol, and alkylated with iodoacetamide. Reduction and alkylation helps prevent polymerization as well as the binding of eosinophilic granular polypeptides to other polypeptides. Total eosinophil counts were determined for each specimen after initial collection and after the indicated processing to assure that iatrogenic lysis of eosinophils was not occurring. The amount of MBP in each patient's mucus sample was assessed using the MBP assay described in Example 5.

Figure 19:
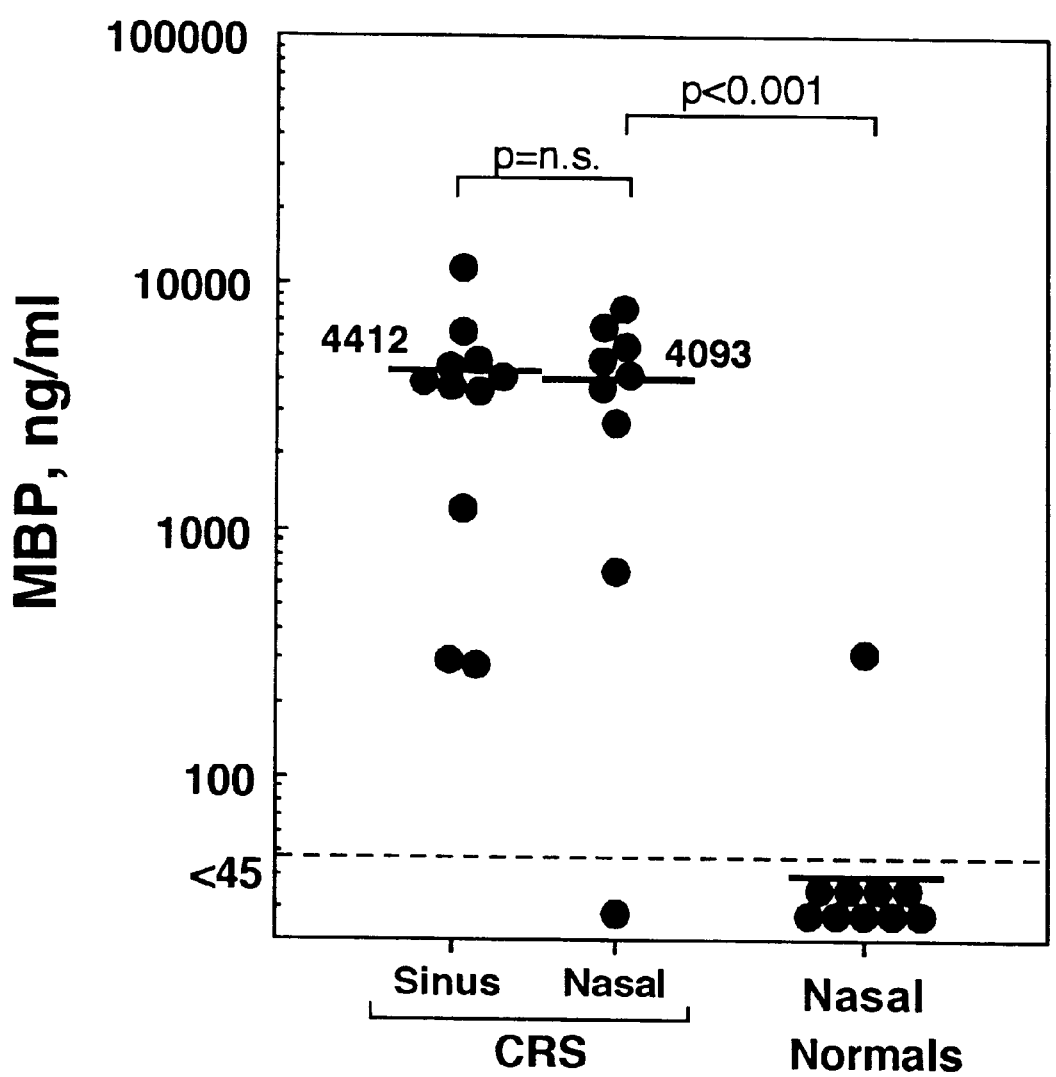
FIG. 19 is a graph plotting the amount of MBP (ng/mL) measured in mucus samples collected from the sinus and nasal cavities of chronic rhinosinusitis (CRS) patients and from the nasal cavities of normal controls.

Mucus samples collected from chronic rhinosinusitis patients contained much more detectable MBP than mucus samples collected from normal controls (FIG. 19). Specifically, the average amount of MBP detected in mucus samples collected from the sinus cavities of chronic rhinosinusitis patients was about 4.4 μg/mL. Likewise, the average amount of MBP detected in mucus samples collected from the nasal cavities of chronic rhinosinusitis patients was about 4.1 μg/mL. These results indicate that the high levels of MBP found to exist in the mucus of chronic rhinosinusitis patients can be detected in mucus collected from both nasal and sinus cavities. The average amount of MBP detected in mucus samples collected from the nasal cavities of normal controls was less than 45 ng/mL. In fact, the amount of MBP detected in the mucus collected from normal controls was below detection in most cases. These results confirm that the amount of MBP within an individual's mucus can be used to identify the existence of chronic rhinosinusitis.

Example 7

Allergic Rhinitis Patients do not Have an Eosinophil Degranulating Condition as Determined by an Immunoassay Mucus samples collected from allergic rhinitis patients and normal controls by nasal lavage were examined using the MBP assay described in Example 5. The nasal lavage was performed with the individual's head tilted back by instilling about 5 mL of normal saline into one nostril followed by bringing the head forward to collect the fluid in a 150 mL beaker. The individual then blew air out of the nostril to collect the maximum amount of fluid. This procedure was performed twice in each nostril using a total of about 20 mL of normal saline. The samples were placed on ice and processed within 2 hours. To process, the nasal lavage fluid was passed through a 42 μm nylon mesh filter (Nitex®, Tetko® Inc., Briarcliff Manor, N.Y.) into a 50 mL conical Sarstedt® tube (Sarstedt, Newton, N.C.), and the filtrate centrifuged at 420*g for 12 minutes at 4° C. After centrifugation, the supernatant was removed, and the pellet resuspended in 100 mL of phosphate-buffered saline (PBS). A portion of the supernatant was stored at −20° C. in vials, while the remainder was concentrated using Centriprep® concentrators (Amicon, Beverly, Mass.) having a molecular weight cutoff of 3,000 Daltons. To prevent surface adsorption of the nasal lavage polypeptides, the Centriprep® concentrators were first treated with 3 mL of 0.2% human serum albumin (HSA) and centrifuged for 10 minutes at 400*g. After decanting the HSA, the Centriprep® was washed with PBS and centrifuged for an additional 10 minutes at 400*g. After removing the PBS, the nasal lavage fluid supernatant was added to the Centriprep® concentrator and centrifuged for about 1 to 2 hours at 400*g until about a 10× concentration was achieved. The concentrated fluid was stored at −20° C. The MBP assay described in Example 5 was used to assess the amount of MBP in the concentrated fluid. To reflect the value of the unconcentrated fluid, each result was divided by ten.

Figure 20:
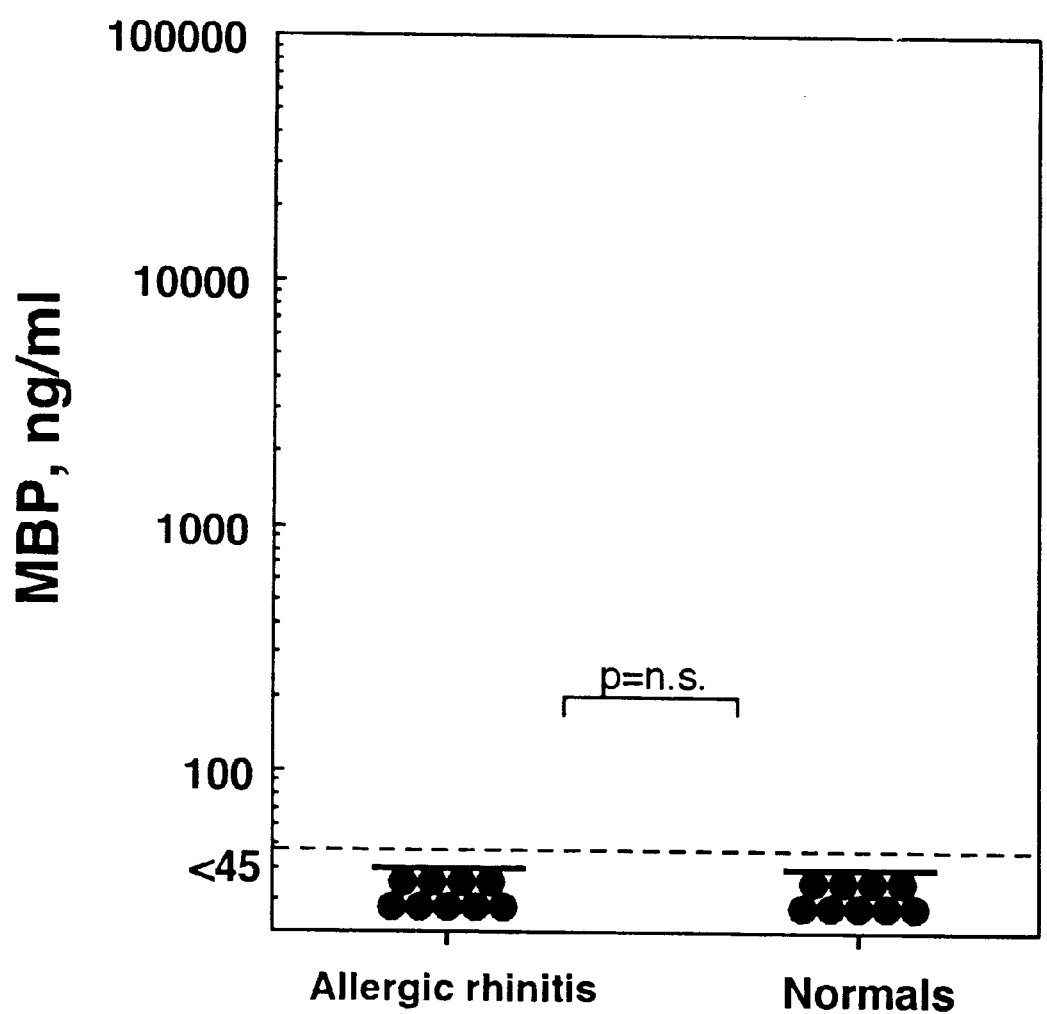
FIG. 20 is a graph plotting the amount of MBP (ng/mL) measured in mucus samples collected from allergic rhinitis patients and normal controls by nasal lavage.

The amount of MBP detected in mucus samples collected from allergic rhinitis patients and normal controls via nasal lavage was below detection (FIG. 20). Specifically, the average amount of MBP detected in nasal lavage mucus samples from each group was less than 45 ng/mL. These results when compared to the results obtained in Example 5 confirm that the amount of MBP within an individual's mucus can be used to distinguish patients having allergic rhinitis and chronic rhinosinusitis. Chronic rhinosinusitis patients have high levels of MBP within their nasal and sinus mucus while allergic rhinitis patients have low levels of MBP, if any, within their nasal and sinus mucus.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for determining whether or not a sinusitis condition in a patient is non-invasive fungus-induced rhinosinusitis, said method comprising:
   a) providing a sample of nasal or paranasal mucus from said patient, and
   b) examining said sample to determine the presence or absence of a concentration of major basic protein within mucus of said patient, wherein said major basic protein is in free form, wherein said concentration is greater than 45 ng per mL mucus of said patient, and wherein said presence of said concentration indicates that said sinusitis condition is said non-invasive fun-us-induced rhinosinusitis, thereby distinguishing said non-invasive fungus-induced rhinosinusitis from other sinusitis conditions.
2. The method of claim 1, wherein said patient is human.
3. The method of claim 1, wherein s aid sample comprises nasal mucus.
4. The method of claim 1, wherein said sample comprises sinus mucus.
5. The method of claim 1, wherein said sample is examined using an immunological assay.
6. The method of claim 5, wherein said immunological assay comprises:
   a) contacting said sample with a capture antibody having binding specificity for major basic protein to form a major basic protein-antibody complex, and
   b) detecting the amount of said complex, wherein the amount of said complex indicates the amount of major basic protein in said sample in a free form, said presence or absence of said concentration being determinable based on said amount.

* * * * *

UNITED STATES PATENT AND TRADEMARK OFFICE
CERTIFICATE OF CORRECTION

PATENT NO.    : 6,416,955 B1
DATED         : July 9, 2002
INVENTOR(S)   : David A. Sherris et al.

It is certified that error appears in the above-identified patent and that said Letters Patent is hereby corrected as shown below:

<u>Column 18,</u>
Lines 13-14, please delete "fun-us" and insert -- fungus -- therefor.

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.          : 6,416,955 B1
APPLICATION NO. : 09/553790
DATED                   : July 9, 2002
INVENTOR(S)        : David A. Sherris et al.

It is certified that error appears in the above-identified patent and that said Letters Patent is hereby corrected as shown below:

Column 1, line 3, please insert

--STATEMENT REGARDING FEDERALLY FUNDED RESEARCH

The following invention was made with government support under Grant No. AI049235. The federal government has certain rights in the invention.--

Signed and Sealed this

Tenth Day of March, 2009

JOHN DOLL
*Acting Director of the United States Patent and Trademark Office*